United States Patent [19]
Van Ooyen

[11] Patent Number: 5,840,528
[45] Date of Patent: Nov. 24, 1998

[54] **TRANSFORMATION OF *PHAFFIA RHODOZYMA***

[75] Inventor: Albert Johannes Joseph Van Ooyen, Vorrburg, Netherlands

[73] Assignee: Gist-Brocades, N.V., Netherlands

[21] Appl. No.: 494,151

[22] Filed: Jun. 23, 1995

Related U.S. Application Data

[63] Continuation of Ser. No. 119,609, Sep. 10, 1993, abandoned.

[30] Foreign Application Priority Data

Sep. 11, 1992 [EP] European Pat. Off. .............. 92202789
Oct. 28, 1992 [EP] European Pat. Off. .............. 92203313
Jun. 25, 1993 [EP] European Pat. Off. .............. 93201848

[51] Int. Cl.$^6$ .............................. C12P 21/06; C12N 1/19; C12N 15/64; C12N 15/11
[52] U.S. Cl. .................... 435/69.1; 435/71.1; 435/172.3; 435/254.2; 435/320.1; 536/23.1; 536/24.1
[58] Field of Search ................... 435/254.1, 254.11, 435/254.2, 69.1, 71.1, 172.3, 243, 320.1; 536/23.1, 24.1

[56] References Cited

FOREIGN PATENT DOCUMENTS 482 544   4/1992   European Pat. Off. .
88/08025  of 0000  WIPO .

OTHER PUBLICATIONS

Miller et al., "*Phaffia*, a New Yeast Genus in the *Deuteromycotina*(*Blastomycetes*)", *Int. J. Syst. Bacteriol.* 26:286–291 (1976).

Phaff et al., "A Comparative Study of the Yeast Florae Associated with Trees on the Japanese Islands and on the West Coast of North America", *Proc. IV IFS: Ferment. Technol. Today* 759–774 (1972).

Johnson et al., "The *Yeast* Phaffia rhodozyma as a Dietary Pigment Source for Salmonids and Crustaceans", *J. Fish. Res. Board Can.* 34:2417–2421 (1977).

Andrewes et al., "Carotenoids of *Phaffia Rhodozyma*, A Red Pigmented Fermenting Yeast", *Phytochemistry* 15:1003–1007 (1976).

Andrewes et al., "(3R,3'R)–Astaxanthin From The Yeast *Phaffia Rhodozyma*", *Phytochemistry* 15:1009–1011 (1976).

Fincham, Microbial Rev., 1989, vol. 53 (1): pp. 148–170.

*Primary Examiner*—George C. Elliott
*Assistant Examiner*—Terry A. McKelvey
*Attorney, Agent, or Firm*—Morrison & Foerster LLP

[57] ABSTRACT

The present invention discloses a transformed Phaffia strain. Also disclosed are specific vectors for transforming Phaffia, preferably such vectors contain expression regulating sequences obtained from Phaffia. The present invention also discloses the use of certain marker genes in Phaffia. The invention further discloses a method for transforming Phaffia.

20 Claims, 8 Drawing Sheets

B=BamHI, Bg=Bgl2, S=SalI, X=XhoI, E=EcoRI, SI=SacI

TRANSFORMATION OF *PHAFFIA RHODOZYMA*

This application is a continuation of application Ser. No. 08/119,609 filed Sep. 10, 1993, now abandoned.

TECHNICAL FIELD

The present invention relates to genetic engineering. More specifically, the present invention discloses means and methods for transforming certain yeast strains and for obtaining overexpression of desired genes in these strains. The present invention discloses transformed *Phaffia rhodozyma* strains. The invention also discloses a method for transforming *Phaffia rhodozyma* strains. Also disclosed are vectors capable of transforming these strains. Said vectors contain expression regulating sequences which are active in Phaffia and which may be obtained from any suitable organism including Phaffia.

BACKGROUND OF THE INVENTION

In 1972 Phaff et al. (Proc. IV IFS: Ferment. Technol. Today 759–774) first described a new yeast species which had been isolated from broad-leafed trees in Japan. This yeast was characterized by its high carotenoid content and the fact that it was the first carotenoid containing yeast found to ferment several sugars. Since all the strains were obtained from mountainous areas in Japan and Alaska, Phaff et al. proposed the name *Rhodozyma montanae*.

In 1976 Miller et al. (Int. J. Syst. Bacteriol. 26: 286–291) attempted to give a more systematic description of this species and proposed the name *Phaffia rhodozyma*.

*Phaffia rhodozyma* is the only species recognized to date in the genus Phaffia.

Careful analysis of the carotenoid content of this yeast has been reported by Andrewes et al. 1976 (Phytochemistry 15: 1003–1007) and Andrewes and Starr 1976 (Phytochemistry: 15 1009–1011). It was found that one of the principal carotenoids in this species is astaxanthin. Astaxanthin was already known to be responsible for color formation in for example krill and hence for the coloring of fish such as trout, salmon and seabream which in nature are reported to feed on krill.

Johnson et al. (1977) (J. Fish. Res. Board Can. 34: 2417–2421) reported the use of Phaffia as a dietary pigment source. They concluded that both salmonids and crustaceans can be colored by Phaffia.

One of the limiting factors for wide-scale application of Phaffia as a fish feed ingredient turned out to be the low astaxanthin content of this yeast.

Danisco (International Patent Application WO 88/08025, meanwhile granted as European patent EP 367 765B) for the first time reported the increased astaxanthin content of Phaffia cells after growth of cells which had been mutagenized.

However, the maximum amount of astaxanthin productivity appears to be limited since after several rounds of mutagenesis no increase in astaxanthin content can be found any longer (as reported in European Patent Application EP 482544). This may partially be due to adverse mutations which occur during random mutagenesis.

Recombinant DNA technology could probably overcome this bottle-neck in strain development. However, in order to be able to obtain recombinant strains one needs an effective transformation process and adequate expression regulating sequences.

Transformation of Phaffia is hampered by the rigid cell wall which also affects the possibility of obtaining Phaffia protoplasts. Furthermore, no genetic tools such as plasmids, promoters, and marker genes are available for Phaffia to date. Recently protoplasting of Phaffia has been reported (EP 482544). These protoplasts could advantageously be used in protoplast fusion experiments and gave rise to strains with increased astaxanthin productivity.

To date no transformation of Phaffia strains has been described.

SUMMARY OF THE INVENTION

The present invention discloses transformed Phaffia strains, preferably transformed *Phaffia rhodozyma* strains.

The present invention also discloses methods for transforming *Phaffia rhodozyma*.

Also disclosed are vectors capable of transforming these strains containing expression regulating sequences active in Phaffia. Preferably, these expression regulating sequences are obtained from Phaffia. In an exemplified embodiment of the invention the actin promoter from Phaffia is used to regulate expression.

In general a Phaffia strain is disclosed transformed with a vector containing a desired gene cloned downstream from a promoter which is active in Phaffia, and optionally a selection marker cloned downstream of a promoter which is active in Phaffia.

One of the methods of the present invention for transforming Phaffia comprises, growing Phaffia cells to the exponential phase, preparing protoplasts from these cells, adding a vector containing a desired gene cloned downstream from a promoter which is active in Phaffia and optionally a selection marker, plating the protoplasts on a selective regeneration medium and selecting the transformed Phaffia strains.

Another method for transforming Phaffia strains is the LiAc method.

The expression regulating sequences can be cloned upstream from both homologous and heterologous genes.

The present invention thus provides means and methods for obtaining expression of desired genes in Phaffia. Phaffia can thus be used for producing heterologous proteins. Through cloning and expression of genes involved in the carotenoid biosynthetic pathway it also becomes possible to use *Phaffia rhodozyma* for obtaining desired carotenoids. Desired carotenoid production includes increased production of astaxanthin also included is production of other carotenoids such as zeaxanthin, cantaxanthin and β-carotene.

━structural actin gene (exons)

═5' upstream and promoter sequence of actin

____ actin intron

→←  oligonucleotides used in the inverse PCR

Figure 3:
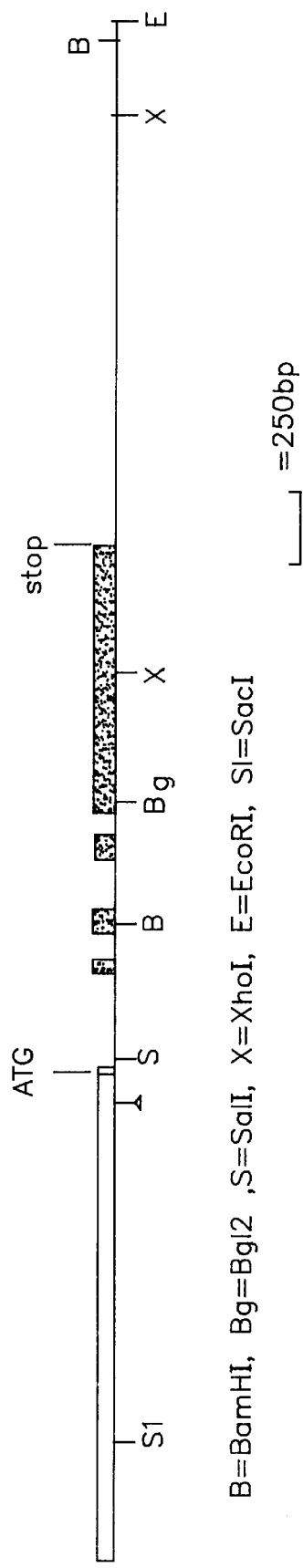

FIG. 3. The organisation of the *Phaffia rhodozyma* actin gene. Restriction sites used for cloning are indicated.

━structural actin gene (exons)

═5' upstream and promoter sequence of actin

____ actin intron

△3' non coding actin sequence

⇞transcription start site

Figure 4:
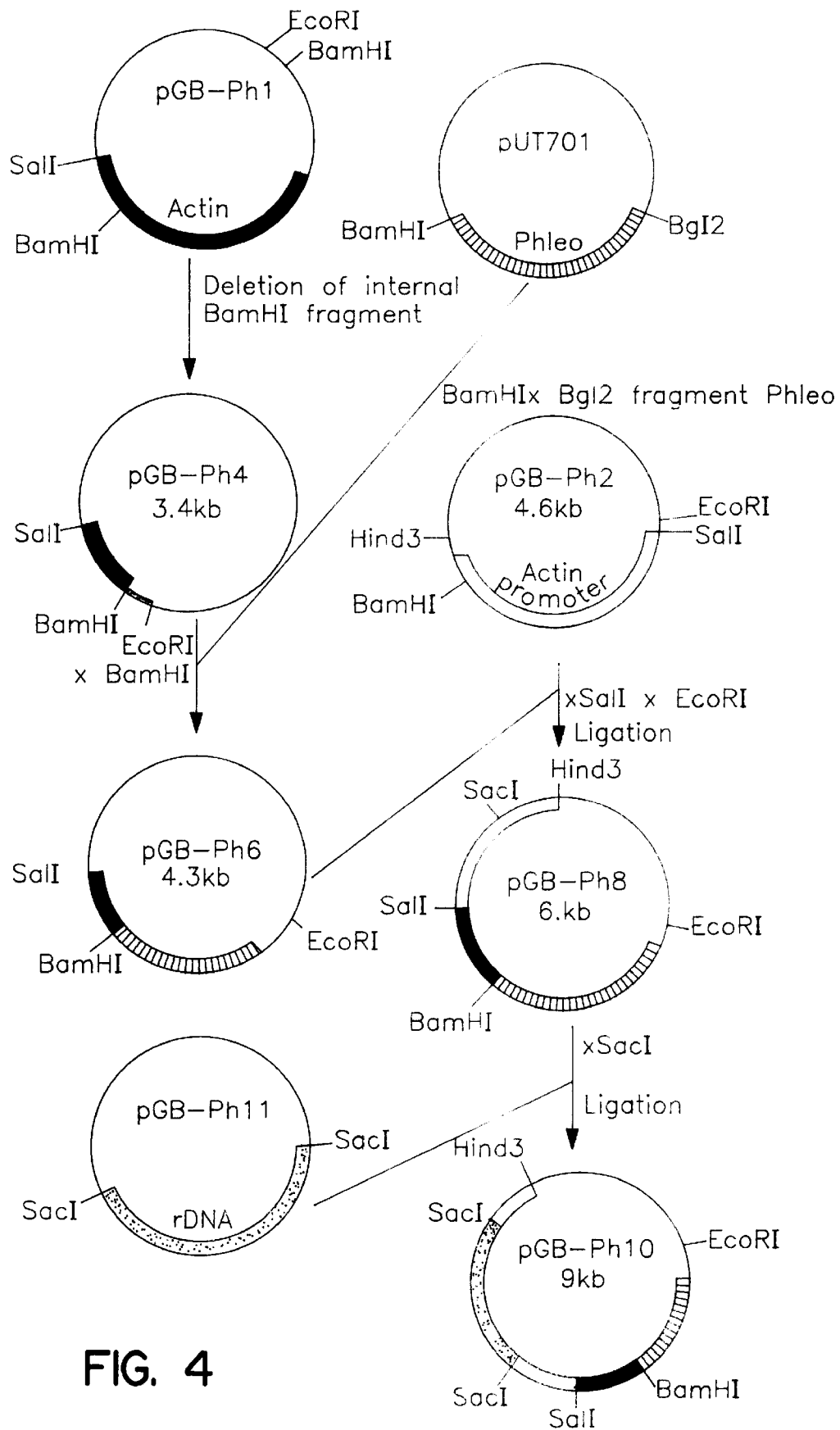

FIG. 4. Cloning diagram of the actin-phleomycin fusion constructs.

═upstream and promoter sequences of *Phaffia rhodozyma* actin

▰▰ribosomal DNA of *Phaffia rhodozyma* actin

━structural actin gene of *Phaffia rhodozyma* actin

▰▰Phleomycin (S.h) gene+cycl(yeast) terminator

━3' non coding *Phaffia rhodozyma* actin sequences

____ pTZ18R

Figure 5:
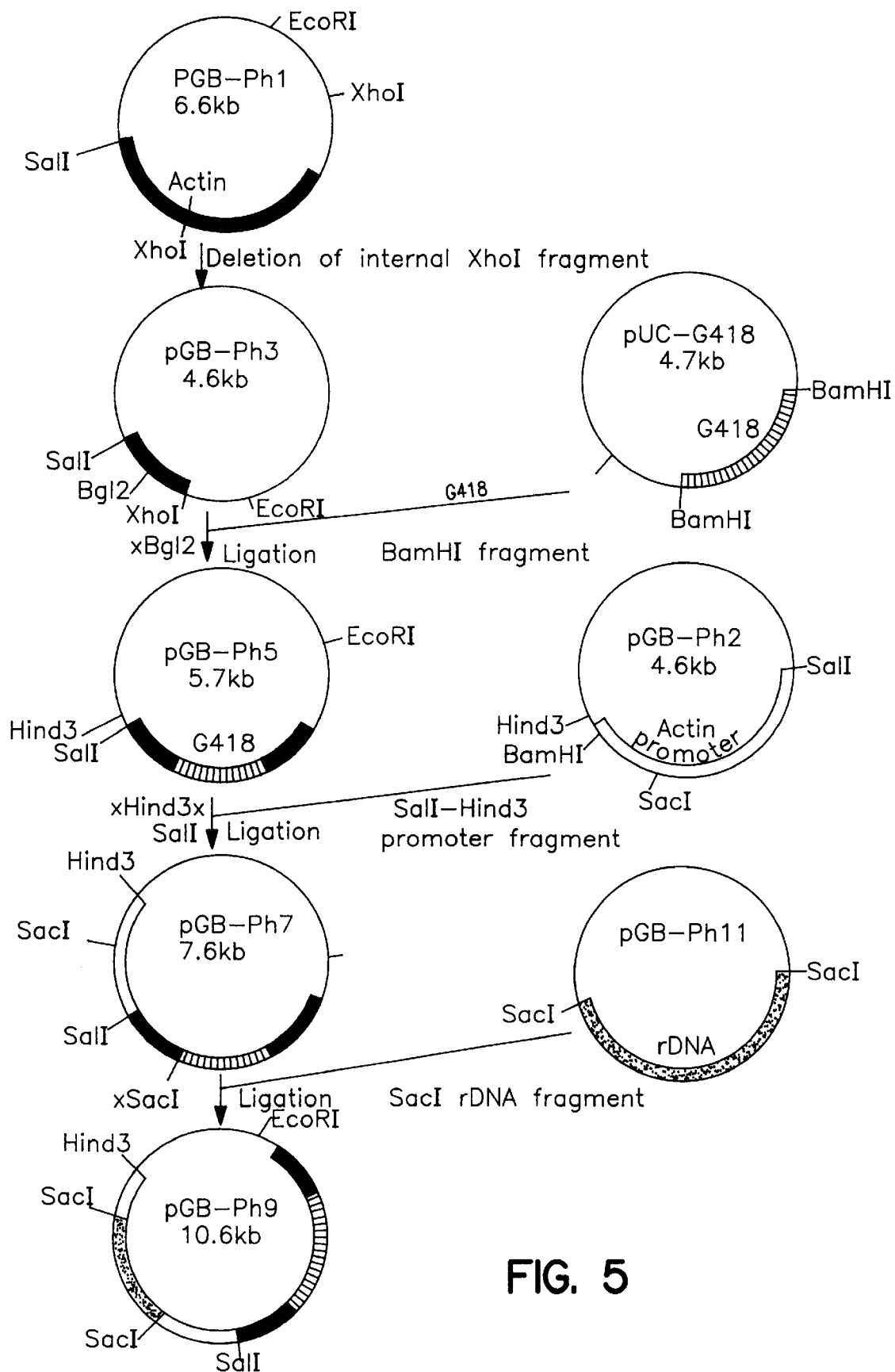

FIG. 5. Cloning diagram of the actin-G418 fusion constructs.

═upstream and promoter sequences of *Phaffia rhodozyma* actin

▰▰ribosomal DNA of *Phaffia rhodozyma* actin

━structural actin gene of *Phaffia rhodozyma* actin

▰▰G418

━3' non coding *Phaffia rhodozyma* actin sequences

____ pTZ18R

Figure 6A:
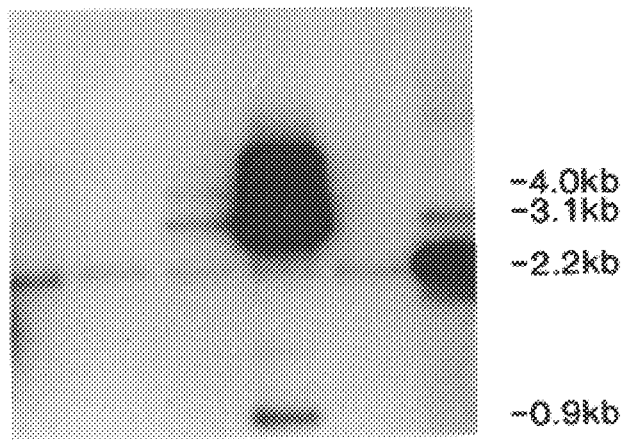
Figure 6B:
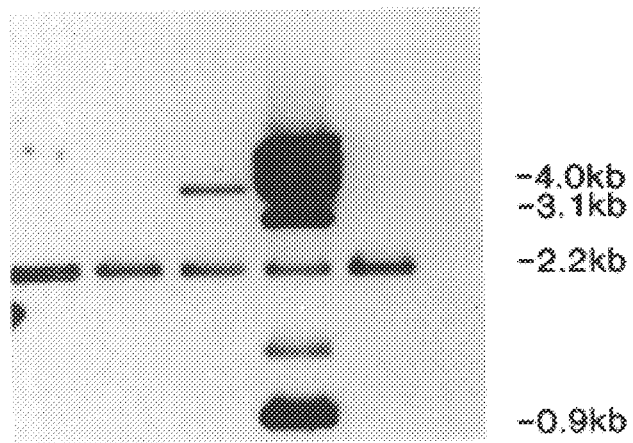
Figure 6C:
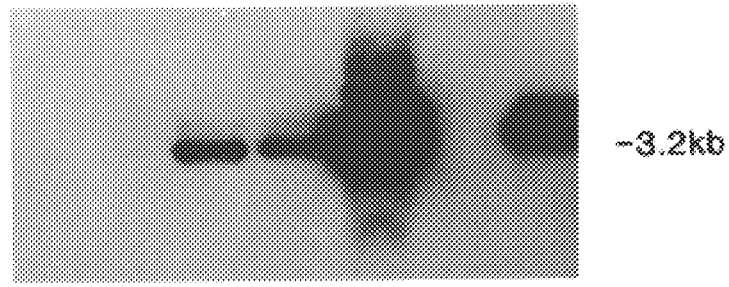

FIG. 6A–6C. Southern blot of chromosomal DNA digested with both BamHI and EcoRI and isolated from transformed Phaffia strains (Example 11) with three different probes i.e FIG. 6A) 430 bp BamHI-StuI Phleo fragment exposed for 72 hours, FIG. 6B) 1.8 kb BmHI-SalI actin promoter fragment exposed for 3 hours, FIG. 6C) pTZ18R exposed overnight.

Figure 7A:
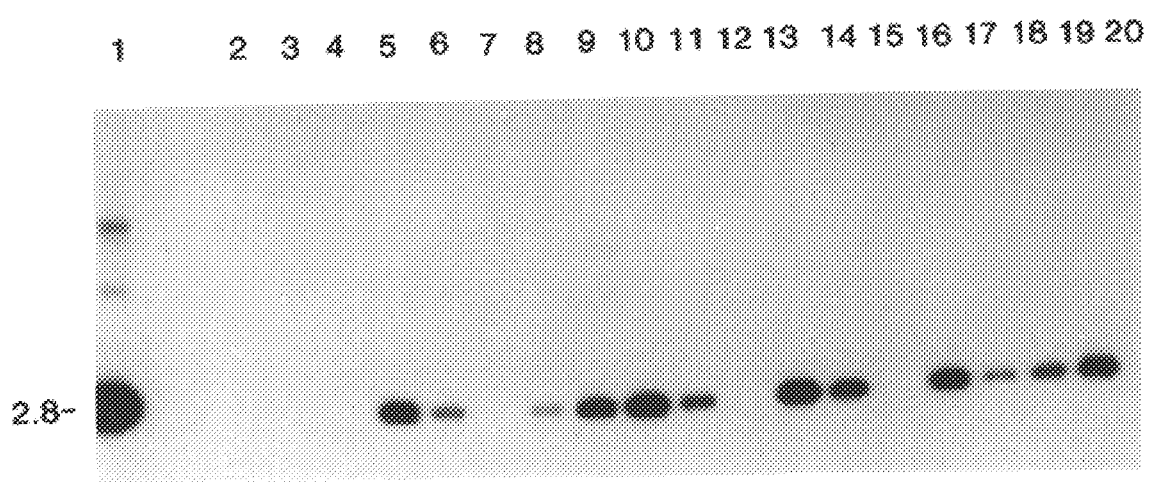

FIG. 7A. Southern blot with BamHI digested chromosomal DNAs of (lane 1 to 20); pGB-Ph9, CBS6938, 1b, 2b, 2c, 2d, 2e, 2f, 2h, 2i, 2j, 3b, 4a, 4c, 4d, 4e, 4f, 4g, 4h, 4i. CBS6938, 1b and 3b are negative controls; pGB-Ph9 is a positive control. The other numbers are possible transformants. Hybridization with PTZ-probe.

Figure 7B:
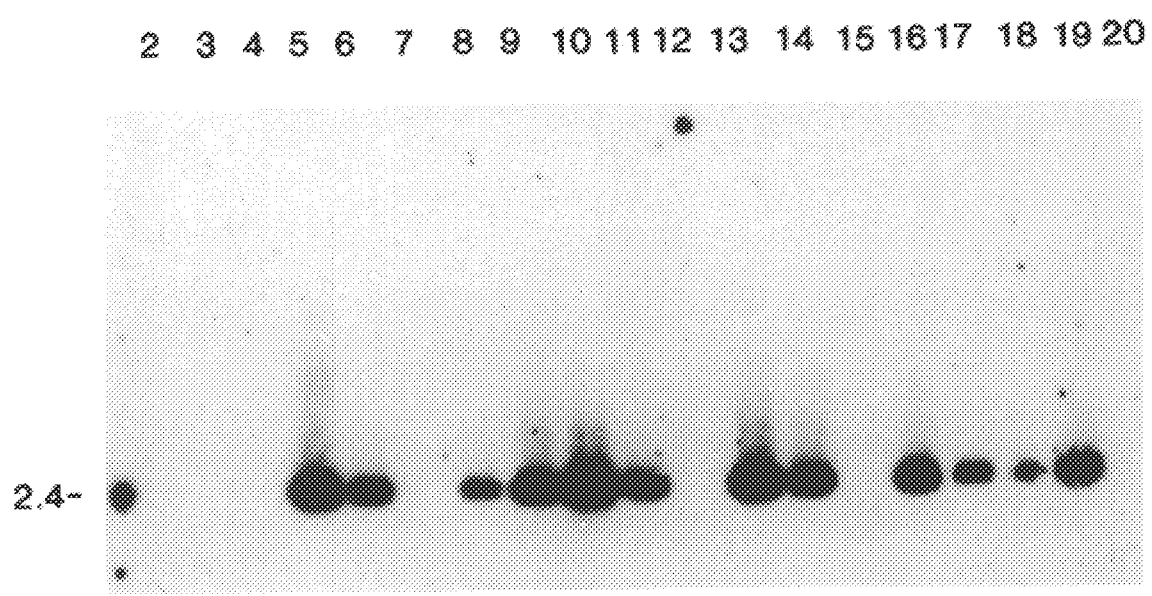

FIG. 7B. See legend of FIG. 7A Hybridization with G418-probe.

Figure 7C:
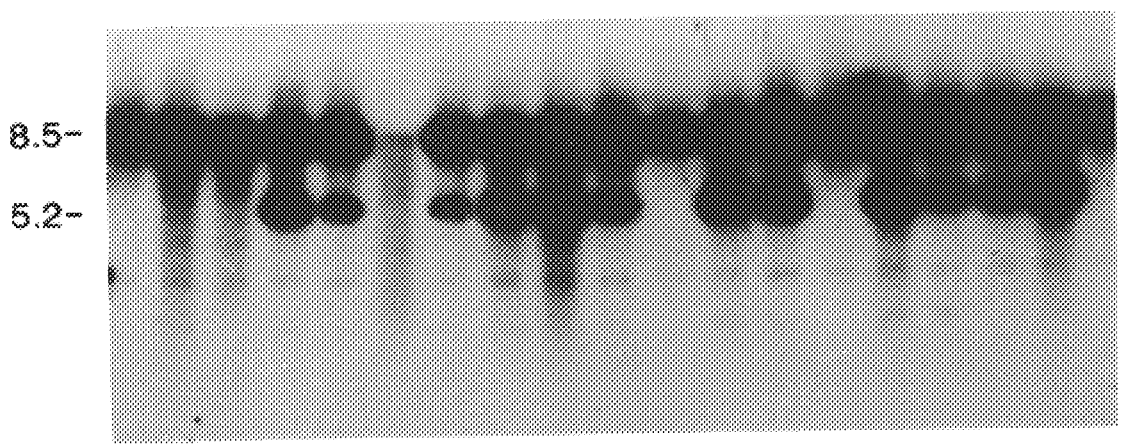

FIG. 7C. See legend FIG. 7A Hybridization with rDNA-probe.

DETAILED DESCRIPTION OF THE INVENTION

In its most general form the present invention describes transformed Phaffia cells. Preferably, the Phaffia cells are *Phaffia rhodozyma* cells. The present invention also describes methods for transforming Phaffia cells.

Although not limited thereto successful transformation is disclosed using a Phaffia promoter cloned upstream from a gene to be expressed.

The present invention further indicates that Phaffia cells, like other yeast cells are sensitive to selection agents such as G418, hygromycin and phleomycin over a reasonable concentration range. Transformation of the Phaffia cells with the genes encoding the proteins conferring resistance to these agents upon the cells provides a suitable selection system for transformation.

The present description contains evidence indicating that the use of strong yeast promoters, preferably promoters obtained from *Saccharomyces cerevisiae* and *Kluyveromyces lactis*, more specifically the ADH1, the GAPDH, and the TEF 1α promoters from *Saccharomyces cerevisiae* do not give rise to the expression of marker genes in transformed Phaffia cells. In fact it thus becomes impossible to prove whether transformation occurred at all.

Other strong promoters have been used like the SV 40 promoter, the kanamycin promoter from Tn903, the PGK promoter from *P. chrysogenum* and the GAPDH promoter from *A. nidulans* all with the same (negative) result.

This prompted the search for promoters from Phaffia. As a general approach genes were selected which are expected to be conserved in yeast species. Probes were isolated representing especially conserved regions in these genes and these probes were used to hybridize Phaffia genomic DNA. Hybridizing fragments corresponding to specific genes were used to isolate the complete genes or at least the promoter regions of the genes. The promoter so isolated was then cloned in a suitable transformation/expression vector upstream from a reporter gene.

Phaffia protoplasts were made using standard procedures and they were subsequently transformed with the transformation/expression vector. Finally, the transformed Phaffia protoplasts were regenerated and selected on an appropriate selective medium.

Other methods can also be employed to isolate Phaffia promoters. Such methods include isolation of an expressed Phaffia protein, sequencing part of this protein and developing an oligonucleotide probe based on this sequence. After hybridizing digested and electrophoresed DNA or screening a genomic- or cDNA Phaffia library a gene can be selected. Subsequently, the promoter of this gene can be localized and cloned in an appropriate way.

The present invention describes the use of the following probes to hybridize with genomic Phaffia DNA;

a 1.7 kb ribosomal DNA fragment from *K.lactis*, a 800 bp PCR-fragment of the TPI-gene of *K.lactis*, a 250 bp PCR-fragment of the *K.lactis* elongation factor;

a 3 kb fragment of the PGK-gene in pTZ18R of *S. cerevisiae*, and a 200 bp PCR-fragment of the 5' coding region of the actin gene of *K.lactis*.

It turned out that only the rDNA and actin fragment hybridized with genomic Phaffia DNA, the TPI, PGK and elongation factor probes, although obtained from highly conserved genes, did not hybridize at low stringency. The genomic DNA containing the actin gene was subsequently cloned and the hybridizing clones were sequenced. The sequence was found to correspond with the known actin sequence from other yeasts. The sequence was subsequently used as a specific probe to detect a clone containing the actin promoter of *Phaffia rhodozyma*. The present invention thus discloses an isolated and purified DNA fragment encoding a Phaffia promoter preferably, the Phaffia actin promoter.

After the promoter had been isolated it was used to clone in an operable manner upstream from a desired gene to be expressed. Such a desired gene can be any gene. Both homologous and heterologous genes can be used. Homologous genes include genes involved in the carotenoid biosynthesis pathway, these genes include structural genes as well as regulatory genes. Heterologous genes include all genes of interest whose expression product are not lethal to Phaffia, such genes include genes encoding pharmaceutical proteins, detergent enzymes, food and feed enzymes and proteins involved in carotenoid synthesis. For ease of detection in the present application heterologous G418 and Phleomycin resistance encoding genes have been used. These genes can be perfectly fused with the desired promoter. It is however also possible to make a fusion with a part of the gene normally following the promoter, resulting in a fusion protein.

Transformation of *Phaffia rhodozyma* was performed in the following manner. Phaffia protoplasts were made using standard procedures and they were subsequently transformed with the transformation vector. Finally, the transformed Phaffia protoplasts were regenerated and selected on an appropriate selective medium.

Transformants were also obtained using the so-called lithium acetate method. In this method cells are incubated overnight in the presence of PEG, Lithiumacetate and transforming DNA. After incubation cells are plated on selective plates. Although applicants are the first to describe transformed Phaffia cells it is recognized that other methods may be applicable for obtaining transformants these methods include electron bombardment.

The present invention discloses for the first time a vector capable of transforming a Phaffia with concurrent expression of the cloned gene. The disclosed vector contains the actin promoter and a marker gene. Using a selection medium transformation of Phaffia was proven. The actin promoter was used cloned upstream from the G418 and Phleomycin resistance encoding genes. The Phaffia promoter may also be used for obtaining expression of other cloned genes. The vector then contains a desired gene and a selection marker gene.

Now that a promoter and a selection system for Phaffia have been developed it becomes possible to clone desired genes in Phaffia. Such genes include all heterologous genes giving rise to useful products upon expression. However, *Phaffia rhodozyma* provides other interesting possibilities.

In the broadest sence the method provided by the present invention makes possible the cloning and expression of cloned heterologous or homologous genes in Phaffia. Said genes may be cloned on an episomal vector or they may be integrated into the genome. Apart from using Phaffia as a production host for desired proteins it is also possible to clone and express the genes involved in the biosynthetic pathway of carotenoids to alter the pathways found in Phaffia or to develop novel pathways to carotenoids not normally accumulated in Phaffia. The resulting transformed cells can produce a carotenoid which is not naturally occurring in Phaffia. It can produce an increased amount of a carotenoid naturally occurring in the host cell.

An example of this is the following. Classical mutagenesis is used to obtain mutants that produce specific precursors for astaxanthin, a preferred example of such a precursor is β-carotene. Other carotenoid precursor producing strain can be obtained in the same way. Subsequently, a gene is introduced into the Phaffia strain of which the expression product uses the precursor accumulated in the strain after classical mutagenesis as a substrate. In the case of β-carotene as a substrate, a suitable gene is for example the gene of which the protein product synthesizes zeaxanthin (crtZ gene) obtained from *Erwinia uredovora* (Misawa et al.1990. J. Bacteriol. 172: 6704–6712) Other such genes can be obtained for example from Flavobacterium (a gram-positive bacterium), Synechococcus (a cyanobacterium) or Chlamydomonas or Dunaliella (algae).

It is also possible to use wild-type strains, without mutagenesis. By overexpression of an enzyme which uses a precursor in a biosynthetic pathway this pathway may be deviated from its natural course and give rise to another carotenoid product not naturally occurring in the used strain.

Cloning and overexpression of genes directly involved in the production of astaxanthin or of genes or sequences having a regulatory function in astaxanthin production can lead to an increased astaxanthin production.

The gene of choice can be expressed episomally or it can be integrated into the genome of the host cell. It may be useful to use gene amplification to obtain several copies of the gene in the host cell. The present examples provide evidence for the presence of an ARS in the rDNA from *Phaffia rhodozyma*.

It is possible to produce other carotenoid precursors in the same way, in general all carotenoids that can enzymatically be derived from precursors of astaxanthin in Phaffia can be obtained, specific carotenoids include cantaxanthine and lycopene. Furthermore, β-carotene can be converted to retinol in a similar way.

The transformed Phaffia cells are cultivated under conditions wherein no alcohol is produced. The temperature is in the range of 15°–26° C. The preferred range is 20°–22° C. The fermentation is performed in a medium comprising suitable nutrients. These include molasses or saccharose is carbon source and nitrogen sources such as urea, ammonium salts or corn-steep liquor. Micronutrients are also included in the medium.

Furthermore, growth is performed under aerobic conditions. Growth conditions, the choice of specific nutrients and substrate limitation have been reported to influence the growth of Phaffia cells. In accordance with the desired product protein or carotenoid growth conditions and precursor addition is adapted.

After culturing the transformed Phaffia cells, the cells are harvested subsequently the cells may be treated in different ways depending on the desired use of the product or on the formulation. Treatments include;

opening the cells, drying the cells, extracting the product, protein or carotenoid from the cells.

The yeast cells containing the carotenoids are used as such or in dried form as additives to animal feed or food.

Furthermore, the yeasts are mixed with other compounds such as proteins, carbohydrates or oils. In general, all methods applied to make Phaffias suitable for addition to feed or food can be used on these transformed strains.

The carotenoids can be isolated for example as described by Johnson et al. (Appl. Environm. Microbiol. 35:1155–1159 (1978)).

Purified carotenoids are used as colorants in food and/or feed. It is also possible to apply the carotenoids in cosmetics or in pharmaceutical compositions.

It is evident from the above description that the examples are only meant as an illustration of a general principle, and are thus not meant to limit the invention in any way.

Experimental

Details of the molecular cloning techniques are described by Sambrook et al. in Molecular Cloning: A laboratory Manual, 2nd edition (1989; Cold Spring Harbor Laboratory Press). These methods include DNA gel electrophoresis, Southern blotting, DNA sequencing, phosphorylation of 5' ends with T4 polynucleotide kinase and synthesis of uniformly labelled DNA probes using random primers.

Enzyme incubations are performed following instructions described by the manufacturer. These incubations include restriction enzyme digestion, ligation.

Strains

*Escherichia coli* JM109 recA1, endA1, gyrA96, thi, hsdR17, supE44, relA1, -, Δ(lacproAB), [F', traD36, proAB, lacIqZΔM15]

*Phaffia rhodozyma* CBS6938

*Phaffia rhodozyma* PF 11-12 was deposited at Centraal Bureau voor de Schimmelcultures, Baarn, The Netherlands under No. CBS 797.91 on 16 Dec. 1991.

Plasmids used for cloning pTZ18R amp R (Pharmacia/LKB)

pUCG418 amp R, geneticin R (EP301670)

pUT701 amp R, phleo R (Cayla)

Media

LB: 10 g/l bacto tryptone, 5 g/l yeast extract, 10 g/l NaCl.

LC⁺plates:

5 g/l yeast extract, 10 g/l bacto tryptone, 8 g/l NaCl, 0.025 g/l Thymine, 1 g/l $MgSO_4.7H_2O$, 4 g/l starch, 20 g/l bacto agar.

YEPD: 10 g/l yeast extract, 20 g/l bacto peptone

2% glucose, when appropriate including Geneticin (G418)

or Phleomycin (plates: +20 g/l bacto agar).

YEPDS:

YEPD +1M Sorbitol (plates: +20 g/l bacto agar).

Other methods

Transformation of *E.coli* was performed using the DMSO procedure, Chung et al. 1989. (Proc. Natl. Acad. Sci. USA. 86: 2172–2175).

Isolation of plasmid DNA from *E.coli* was performed using the Qiagen™ kit.

Isolation of chromosomal DNA from Phaffia is described in Example 3.

Isolation of total RNA from Phaffia was performed according to Lacy, R. L. and R. C. Dickson. 1981. Mol. Cell. Biol. 7: 629.

Colony lifting and hybridization was performed according to the Colony/Plaque Screen™ manual (NEF-978 Du Pont).

DNA fragments were isolated from agarose using Geneclean™.

Polymerase chain reaction (PCR)

PCR reactions were routinely performed in mixtures having the following composition:

1 µg chromosomal DNA or 5 µg total RNA,

1 µM of each oligonucleotide probe,

200 µM of each dNTP, 11 mM Tris-HCl pH 8.3, 50 mM KCL, 2 mM $MgCl_2$, 0.01% w/v gelatin, 1 mM NaCl, 0.1 mM EDTA, 5 U ampli Taq-polymerase (Perkin-Elmer)

In a total volume of 50 µl.

Before adding the Taq-polymerase the DNA is denatured for 8 min. at 94° C. Then Taq-polymerase is added and a drop of mineral oil is added against evaporation. Subsequently the run is started.

Different variants of the PCR method are used. With chromosomal DNA as a template the following run is used; 25 cycli: 2' 94° C., 2' 45° C., in 5' to 72° C., 3' 72° C.

The inverse PCR is the second PCR method used in this method the template DNA is first digested and ligated before it is used in the PCR. The PCR itself is performed as follows; 25 cycli: 2' 94° C., 2' 55°, 3' 72°.

The third PCR method is the reverse transcriptase PCR (RT-PCR) method. Total RNA is used as a template and before the PCR starts a reverse trancriptase reaction must take place. RNasin (20 U) and M.MLV Reverse Trancriptase (50 U) are added to the normal reaction buffer. First the mixture is incubated at 50° C. for 8 min, then the reverse transcription takes place. The denaturation step is performed as usual and after adding the Taq-polymerase the normal PCR run can take place for 25 cycli: 1' 94° C., 1' 55° C., 1' 30" 72° C.

Transformation of Phaffia yeast with lithium chloride was performed according to Ito, H. and Y. Fukuda. J. Bacteriol. 153: 163–168.

Transformation of Phaffia yeast with lithium acetate (PLATE-method) was performed according to Elble R. 1992. Biofeedback 13 No. 1 (Obtainable through Reader Service under no. 118), as described below.

Solutions:

1M $LiAc.2H_2O$ (Sigma), 13.8 g/100 ml, 15' 110° C.

45% PEG 4000 (Brocacef), 90 g/200 ml, 15' 110° C.

PLATE 90 ml 45% PEG 4000

10 ml 1M LiAc 1 ml 1M Tris.HCl pH 7.5

0.2 ml 0.5M EDTA

Procedure:

1 Take 0.5 ml of culture (see background) and spin 10" in a microcentrifuge. Decant supernatant by inverting the tube and shaking it once.

2 Add 10 µl of carrier DNA (100 µg sheared herring sperm DNA) and 1 to 10 µg transforming DNA. Subject to vortex mixing.

3 Add 0.5 ml PLATE. Subject to vortex mixing.

4 Incubate overnight at room temperature on the benchtop (see background).

5 Spread mixture directly on selective plates (see background).

Background:

1 The volume to spin depends on the optical density of the culture. Best results are obtained if $10^7$ cells are used.

4 At least overnight. Take controls for the survival of the cells (survival curve).

5 Plating more than 0.2 ml transformation mixture per selective plate slows the growth of colonies because of the PEG solution.

RNA analyses by 5' primer extension was performed according to Mertins, P. and D. Gallwitz. 1987. (EMBO J. 6: 1757–1763).

Briefly, an amount of 5 µg of total cellular RNA was precipitated together with ±$10^6$ c.p.m. of the appropriate $^{32}$P-end-labelled primer, washed with 70% EtOH, dried and dissolved in 15 µl 50 mM Tris-HCl, pH8.3, 150 mM KCl, 7 mM $MgCl_2$, 0.5 mM EDTA. After heating for 2 min at 65° C., the nucleic acids were kept on ice for 2 min and, after adding 15 U RNasin, 5 µl dNTP's and DTT (0.5 mM each of dATP, dCTP, dTTP and dGTP; 1 mM DTT, final concentration) and 200 U M.MLV reverse transcriptase, the reaction was allowed to proceed for 2 h at 42° C. At the end of the reaction the reaction mix was stored at −20° C. The 5' primer extension reaction products were analyzed on a denaturing polyacrylamide gel.

DNA isolation from gel by agarase treatment was performed as follows:

The DNA band of interest is cut out of a 1% LGT agarose gel and the weight is estimated. The gel slice is incubated in 10 volumes of TE (10 mM Tris-HCl pH 7.5, 1 mM EDTA)

during at least one hour and subsequently equilibrated against TNE (100 mM Tris-HCl pH 7.5, 100 mM NaCl, 1 mM EDTA). The gel slice is melted at 65° C. during 10 minutes and placed in a 37° C. waterbath. After cooling down to 37° C., agarase (Sigma) is added to a concentration of 1 unit per 100 mg of agarose.

The tube is incubated at least for 2 hours at 37° C., preferably overnight, followed by 4× dilution to decrease the salt concentration and extracted with an equal volume of phenol-chloroform (adding first a ½ volume of phenol, vortexing and then adding a ½ volume of chloroform). The extraction is repeated until the interface has disappeared.

Finally a last extraction is done by ½ volume of chloroform and the supernatant is precipitated by adding 1/10 volume of 3M sodium acetate and two volumes of −20° C. ethanol. After incubation at −20° C. for 2 hours the DNA is pelleted by centrifugation, dried and dissolved in a suitable volume of TE.

EXAMPLES

Example 1

Drug Sensitivity of *Phaffia rhodozyma*

A derivative of *Phaffia rhodozyma* strain CBS 6938, PF 11-12, was tested for sensitivity to several drugs. G418, hygromycin and phleomycin were used. Experiments were carried out with fresh overnight YePD (1% yeast extract, 2% peptone, 2% dextrose) cultures. Cells were plated in different amounts on YePD agar plates containing the above-mentioned drugs. G418 was selective in a range of 5 to 20 $\mu$g/ml. Hygromycin in a range of 2.5 to 10 $\mu$g/ml and phleomycin in a range of 0.1 to 0.4 $\mu$g/ml.

*Phaffia rhodozyma* strain CBS 6938 was also tested for sensitivity to G418 and phleomycin. G418 was selective in a range of 5 to 100 $\mu$g/ml and phleomycin in a range of 0.1 to 2.5 $\mu$g/ml.

Example 2

Protoplast Transformation of *Phaffia rhodozyma* using Heterologous Promoters

A derivative of *Phaffia rhodozyma* strain CBS 6938, PF 11-12 obtained by classical mutagenesis, was inoculated in 100 ml liquid medium containing 2% dextrose, 1% yeast extract and 2% peptone (YePD) and grown at 21° C. to an optical density of 0.3–0.8 at 600 nm (ie about 5×10$^6$ cells/ml). Cells were harvested by centrifugation at 5000 rpm (Hettich Rotana) during 5 minutes at room temperature and washed two times with 0.7M KCl-10 mM citric acid pH 6.2. Cell pellets were resuspended in 5 ml of the wash mix and Novozym™ 234 was added to a final concentration of 2 mg/ml. Cells were incubated at 25° C. during 20–40 minutes (strain dependent). Protoplast formation was verified by microscopic analysis. The protoplasts were thoroughly washed in 1M sorbitol and resuspended in 2 ml 1M sorbitol containing 50 mM calcium chloride. 10–25 $\mu$g of undigested plasmid DNA, as described in Table 1, were added to 200 $\mu$l protoplasts and incubated for 10 minutes at room temperature. Experiments were carried out both in the presence and absence of carrier DNA. Subsequently, 2 ml of a solution containing 20% to 40% PEG 4000 and 50 mM calcium chloride were added, mixed thoroughly, and incubated for another 10 to 20 minutes at room temperature. Protoplasts were centrifuged at 300 rpm (Heraeus Biofuge) for 3 minutes at room temperature and the pellet was resuspended in 0.2 ml 1M sorbitol.

Different amounts were plated on filters placed on top of osmotic (1M sorbitol) stabilized YePD agar plates to obtain regeneration. Different regeneration times were used e.g. 4 and 24 hours before transferring the filters to stabilized (1M sorbitol) selective YePD agar medium.

Plasmids based on the PTZ 18/19 backbone were used to transform a derivative of *Phaffia rhodozyma* strain CBS 6938 (PF 11-12 obtained by classical mutagenesis). The reporter genes, present in the plasmids, have been successfully used in transformation and selection studies in many different organisms. We used the kanamycin (G418) resiastance genes from transposons Tn 5 and Tn 903, the hygromycin resistance gene from *E. coli* and the phleomycin resiatance gene from *S. hindustanus*.

The reporter genes were cloned downstream of promoter sequences heterologous with Phaffia e.g. the *S. cerevisiae* ADH 1, GPDH and TEF 1a promoters, the SV 40 promoter, the *E. coli* kanamycin promoter from Tn 903, the *P. chrysogenum* PGK promoter and the *A. nidulans* GAPDH promoter. Plasmids were isolated and purified according to the Qiagentm method from Stratagene™.

Transformation experiments with Phaffia were performed with different DNA samples, i.e. CCC form CsCl purified DNA, SacI liniarized DNA and a pool of existing CCC form plasmids purified by Qiagen columns. The existing plasmids contained different combinations of heterologous promoter sequences with the phleomycin gene (Table 1).

TABLE 1

Summary of existing plasmids used in protoplast transformation experiments.

| plasmid | marker gene | promoter | source of promoter |
|---------|-------------|----------|--------------------|
| pDD 08 | phleomycin | IPNS | Penicillium |
| pAN 8-1 | | GPD | Aspergillus |
| pUT 771 | | ? | Trichoderma |
| pRB 03 | | PGK | Penicillium |
| pUT 332 | | TEF-1α | Saccharomyces |
| pTZHyg B | hygromycin B | GAPDH | Saccharomyces |
| pAN 7-1 | | GAPDH | Aspergillus |
| pUC G418 | geneticin | ADH 1 | Saccharomyces |
| pCR 1 | (G418) | Tn 903 | *E. coli* |
| pSV 2 | | SV 40 | virus SV 40 |

The first experiments with these plasmids, in which we used bilayer plates for selection, protoplasting periods of 30 minutes and the indicated strain, did not reveal a clear difference in colony numbers between control plates and transformation plates (results not shown) and after analysis of a number of potential transformants we were not able to demonstrate transformation.

None of the above-mentioned transformation experiments resulted in colonies resistant to G418, hygromycin or phleomycin. It could be concluded that no (detectable) transformants had been obtained.

This prompted a new approach based on the use of a promoter (and other expression regulating sequences) homologous to Phaffia.

Example 3

Hybridization to Detect Genes from *Phaffia rhodozyma*

*Phaffia rhodozyma* cells (strain CBS 6938) were grown in 100 ml medium containing 2% (w/v) glucose, 1% (w/v) yeast extract and 2% (w/v) bacto-peptone (YePD) at 20° C.

The cells were harvested, after 3 days (OD$_{600}$=±5), by centrifugation. The pellet was resuspended in 20 ml lysis buffer (60 mM EDTA, 1.2M sorbitol, 100 mM Na-citrate pH 7.0) and Novozyme™ 234 was added to a final concentration of 2 mg/ml. The mixture was incubated at 30° C. for approximately 3 hours during which protoplast formation was verified by microscopical analysis. The protoplasts were harvested by centrifugation for 5 minutes at 4000 rpm (Heraeus, Minifuge RF) and the pellet was resuspended in 10 ml 50 mM Tris.HCl pH 7.0; 20 mM EDTA. Subsequently SDS was added to a final concentration of 1%. After lysis of the cells and subsequent fourfold dilution in TE, several phenol/chloroform extractions were performed. The DNA was precipitated with 0.1 volume 3M NaAc and 2 volumes cold ethanol. The DNA was collected by spinning it onto an inoculation needle and was dissolved in 4 ml H$_2$O. After RNase treatment, the solution was extracted several times with phenol/chloroform. The DNA was again precipitated with 3M NaAc and ethanol and dissolved in 3 ml H$_2$O.

Chromosomal DNA was isolated from different species; *K. lactis* and *S. cerevisiae* (Cryer et al. (1975) Methods in Cell Biology 12: 39, Prescott D. M. (Ed.) Academic Press, New York), Penicillium (Bainbridge et al. (1990) FEMS Microbiol. 66: 113–118) and from *Phaffia rhodozyma* CBS 6398 as described above. The isolated DNA was digested with HindIII. The DNA fragments were separated on a 0.7% agarose gel and blotted to nitrocellulose filter. The blots were hybridized in 6+SSC, 0.1% SDS, 5×Denhardts, 100 μg/ml herring-sperm-DNA at 50° C.

The following probes were used on separate blottings;
ribosomal DNA *K.lactis* 1.7 kb ClaI DNA-fragment from (18S) pG7-rDNA#4 (Maleszka and Clark-Walker. 1990. Nucl. Acids Res. 18: 1889).
TPI-gene (Triose Phosphate Isomerase) *K.lactis* 800 bp PCR-fragment (oligo's: 2192–2193, SEQ ID NO: 1 and 2)
KLef-gene (*K.lactis* elongation factor) *K.lactis* 250 bp EcoRI-PvuII DNA fragment from pTZ18RKlef (see below)
PGK-gene (PhosphoGlycerate Kinase) *S.cerevisiae* 3 kb HindIII DNA-fragment from PGK-2 (see Hitzeman et al. 1982. Nucl. Acids Res. 10: 7791–7808).
Actin-gene *K.lactis* 200 bp actin PCR-fragment (oligo's 2557–2558, SEQ ID NO: 3 and 4).

The *K.lactis* elongation factor was cloned as follows. Chromosomal DNA was isolated from *K.lactis* and digested with HindIII. The digested DNA was cloned in pUC13x HindIII and the ligation mix was transformed to *E.coli*. The *E.coli* colonies were screened by colony hybridization, using the EF-lalpha sequence from *S.cer.* as a probe. Specifically the probe was a 4 kb StuI DNA fragment from plasmid pYEF46 (Nagata, S. et al. 1984. EMBO J. 3: 1825–1830). The EF from *K.lactis* was found on a 3.5 kb insert in pUC13, clone pKLEF52. A 350 bp HpaI-EcoRI fragment from the coding region of KLEF from pKLEF52 was cloned in the HindIII (filled in)—EcoRI site of pTZ18R leading to the pTZ18RKlef from which the 250 bp EcoRI-PvuII DNA fragment was used as a probe.

The *K.lactis* actin 200 bp PCR DNA fragment was synthesized with oligonucleotides based on the published sequence of the actin gene of *K.lactis* (Deshler J. O., Garrett P. L. and Rossi J. J. (1989), *Kluyveromyces lactis* maintains *Saccharomyces cerevisiae* intron-encoded splicing signals. Mol. Cell. Biol. 19: 2208–2213). Specifically, the actin oligonucleotides correspond with bp 830–847 and 1011–1030 of the published *K. lactis* sequence.

The DNA fragments were $^{32}$p labelled by random DNA priming. The probes were used on separate blottings. Several hybridization and washing temperatures were used, resulting in different signals on the films depending on the probe used.

After overnight hybridization, the blottings were washed with 3×SSC at room temperature. The autoradiographs were exposed for 3 days with 2 intensifying screens at −80° C.

The only strong hybridization signal on film after exposure was found when the 1.7 kb ribosomal DNA fragment was used as a probe.

The probes (TPI, KLef and PGK) gave no hybridization signal with Phaffia DNA after non-stringent hybridization (3×SSC, 5×Denhardts, 0.1%SDS, 100 μg/ml herring sperm DNA at room temperature) and washing (1×SSC, 0.1%SDS at room temperature).

The films showed that the 200 bp actin sequence of *K. lactis* gave a weak specific signal in the lane with Phaffia chromosomal DNA. The blot hybridized with the actin gene fragment showed the following bands in order of diminishing intensity. The expected 1.3 kb actin band of *K.lactis*, an >10 kb band of *S.cerevisiae*, a 7–8 kb band of Phaffia, a 6 kb band of Penicillium. Bands of different intensity were obtained which can be ascribed to the differences in identity with the *K.lactis* actin probe.

Using the PCR-technique an attempt was made to make a 100% homologous probe. oligonucleotides based on the conserved regions in the GAPDH-gene, TPI-gene and actin gene were used to synthesize a PCR-fragment with chromosomal DNA of Phaffia as a template.

None of the oligo-sets gave rise to a DNA fragment showing specific hybridization.

Example 4

Cloning of the *Phaffia ribosomal* DNA fragment

Ribosomal DNA is often used as an integration site after transformation (Szostak J. W. and R. Wu. (1979). Plasmid 2: 536 and Lopes et al. (1989) Gene 79: 199–206). Therefore we decided to clone the hybridizing ribosomal DNA fragment. A Southern blot was made with Phaffia DNA digested with several restriction enzymes. Chromosomal DNA digested with SacI gave a hybridization signal of a DNA fragment with a length of ±3 kb using rDNA from *K.lactis* as a probe. A chromosomal DNA fraction digested with SacI was ligated with pUCG418 digested with SacI. The ligation mixture was transformed to competent *E.coli* JM109 cells. Several pUCG418 plasmids with ribosomal Phaffia DNA inserts could be detected after colony hybridization of transformants using the 1.7 kb ClaI ribosomal DNA fragment of *K.lactis* as a probe. The plasmid pUCG418 with the 3 kb insert of ribosomal Phaffia DNA is named pGB-Ph11.

Example 5

Cloning of the Actin Gene from Phaffia

Chromosomal DNA isolated from *Phaffia rhodozyma* strain CBS 6938 was digested with several restriction enzymes. The DNA fragments were separated, blotted and hybridized as described before. The autoradiograph was exposed for 16 hours at −80° C. with 2 screens. The film showed DNA fragments of different length digested by different restriction enzymes which hybridize with the 200 bp PCR-fragment of the *K. lactis* actin gene.

Chromosomal DNA digested with EcoRI and SalI gave a hybridization signal of a DNA fragment with a length of 3.8 kb.

A chromosomal DNA fraction of 3.5–4.5 kb digested with EcoRI and SalI was isolated from a 0.7% agarose gel and ligated with PTZ18R digested with EcoRI-SalI. The ligation mixture was transformed to competent *E.coli* JM109 cells. The cells were plated on LC$^+$-agar with 100 μg/ml Amp and 0.1 mM IPTG, 50 μg/ml X-gal. Duplicate filters of the white colonies were prepared and screened with the 200 bp fragment of *K.lactis* actin gene using hybridization and washing conditions similar to those used for Southern blot hybridizations.

Several positive colonies could be detected. The insert in pTZ18R of one clone was partially sequenced. One of the clones was found to contain a part of the actin gene of *Phaffia rhodozyma* based on sequence comparison with known actin genes. The pTZ18R clone with the 3.8 kb Phaffia insert is called pGB-Ph1, the sequence of the insert is given in the sequence listing (SEQ ID NO: 13, wherein the SalI site starts at position 587 and the EcoRI site at 4315). The 3.8 kb EoRl-Sall fragment cloned in plasmid pTZ18R in *E.coli* JM109 was deposited at the Centraal Bureau voor de Schimmelcultures in Baarn, The Netherlands on 5 Oct. 1992, under deposition number CBS 442.92.

The cloned sequence did not contain the 5' part of the actin gene and its promoter as shown by comparison of the DNA sequence with known actin gene sequences (Deshler at al. 1989. Mol. Cell. Biol. 2: 2208–2213 and NG R., and J. Abelson. 1980. Proc. Natl. Acad. Sci. USA. 77: 3912–3916). Therefore we decided to pick up and clone another DNA-fragment at the 5' end of the gene clone, the actin promoter clone.

Example 6

Cloning of the Phaffia Actin Promoter by Inverse PCR

Chromosomal DNA from *Phaffia rhodozyma* (strain CBS6938) was digested with XhoI. An amount of 100 ng total chromosomal DNA x XhoI was ligated in a volume of 50 μl with 1.9 U T4 ligase (BRL) in ligation buffer (BRL). The ligation mix was concentrated by ethanol precipitation and the DNA was dissolved in 10 μl H$_2$O.

Figure 1:
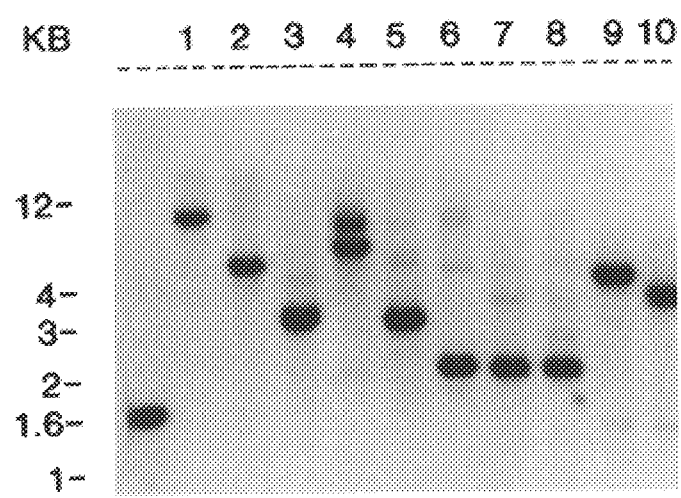
FIG. 1. Mapping of the restriction sites around the Phaffia actin gene. Southern blot of chromosomal DNA digested with several restriction enzymes and hybridized with the 500 bp SalI-BamHI Phaffia actin gene fragment. Lane 1, chromosomal DNA x HpaI; 2, x KpnI; 3, x XhoI; 4, x XbaI; 5, x EcoRV; 6, BamHI; 7, x EcoRI/BamHI; 8, x HindIII/BamHI; 9, x HindIII/BglII. The blot was hybridized in 6×SSC, 5×Denhardts, 0.1% SDS, 100 ng/ml herring sperm DNA at 65° C. and washed with 1×SSC/0.1% SDS at 65° C.

The XhoI digestion was chosen on the basis of the data of the restriction map of the cloned actin gene of Phaffia and hybridization studies of digested chromosomal DNA (FIG. 1).

Figure 2:
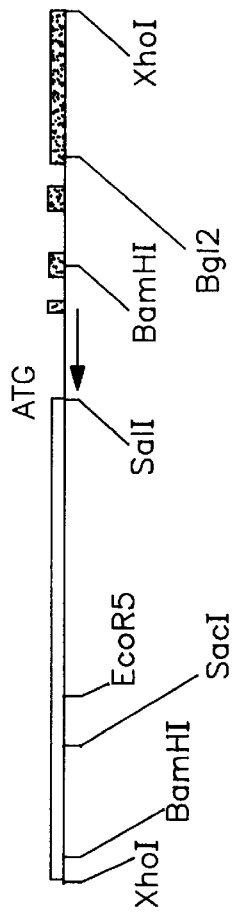
FIG. 2. Restriction map of the 5' site of the Phaffia actin gene. Indicated are the oligonucleotides designed for the inverse PCR.

The XhoI digested DNA, when hybridized with the 500 bp SalI-BamHI fragment of the actin clone, resulted in a 3.1 kb hybridizing band. The 3.1 kb XhoI band consists of a known SalI-XhoI fragment of 1.4 kb and a 1.7 kb fragment 5' flanking the SalI-site. Oligo's were designed on the basis of the known sequence, one 60 bp downstream the SalI-site and the other one 60 bp upstream XhoI-site (FIG. 2).

Phaffia DNA was digested with XhoI, phenol extracted, precipitated with EtOH and dissolved to a concentration of 50 μg/ml. A total of ≦100 ng in 50 μl was ligated over the weekend at 14° C. and used as a starting material for the PCR reactions.

In the inverse PCR (Polymerase Chain Reaction) we used 10–40 ng XhoI digested and ligated chromosomal DNA and 0.5 μg of each oligo (no: 3390, 3391, SEQ ID NO: 5 and 6). The PCR was performed as described above, the PCR conditions were 2 min. 94° C., 2 min. 55° C., 3 min. 72 ° C., for 25 cycles and another elongation step for 7 min. 72° C.

A PCR product with the expected length of 1.8 kb was found. The DNA was isolated from a low gelling point agarose gel with the Magic PCR prep kit (Promega). The DNA was digested with SalI and XhoI and ligated into the SalI-site of PTZ18R. The ligation mixture was transformed to competent *E.coli* JM109 cells. Preparation of the competent cells was performed with the DMSO-method and the cells were plated on LC$^+$-plates with 100 μg/ml Amp and 0.1 mM IPTG/50 μg/ml X-gal. Plasmid DNA was isolated from white colonies and the inserts were mapped by restriction analysis. The clone pGB-Ph2 with the actin promoter fragment was partially sequenced (Sequence listing, SEQ ID NO: 13 from start to SalI site at position 587).

The actin gene and promoter were cloned in two fragments. The actin promoter fragment ends with a SalI site and the actin gene fragment starts with a SalI site. Because we did not clone the flanking sequences of this SalI site, we were not sure that there is only one SalI site. It is possible that there are two or more SalI sites on a short piece of sequence. To be sure that this is not the case we cloned the SalI flanking regions by performing a PCR on chromosomal DNA. Two oligo's (no: 3457, 3475, SEQ ID NO: 7 and 8) were used that amplified a 660 bp chromosomal DNA fragment (FIG. 2). This PCR product was cloned blunt in the SmaI site of PTZ18R and sequenced. The sequence showed us that there is only one SalI site and that the promoter and gene clone match perfectly.

Example 7

Characterization of the Actin Gene

The actin promoter and gene are present on a 5.6 kb cloned Phaffia DNA sequence. On the basis of homology with *K.lactis* and *S.cerevisiae* actin sequences (Deshler at al. 1989. Mol. Cell. Biol. 9: 2208–2213 and NG R., and J. Abelson. 1980. Proc. Natl. Acad. Sci. USA. 77: 3912–3916). and the known splice site consensus (Rambosek, J. and J. Leach. 1987. Crit. Rev. Biotechnol. 6: 357–359 and J. L. Woolford. 1989. Yeast 5: 439–457), the introns and the possible ATG start site were postulated. To confirm these suppositions a 5' primer extension experiment (see Experimental) was performed on Phaffia RNA with the $^{32}$p labelled oligo no: 3457 (SEQ ID NO: 7) and on *S.cerevisiae* RNA with actin oligo no: 3538 (SEQ ID NO: 10) as a positive control. The primer extension products were analyzed on a sequence gel next to a known sequence. On the basis of the length of the known sequence, the length of the primer extension products can be calculated. The positive control *S.cerevisiae* was found to have a length of 185 bp in front of the ATG. A length of 140±30 bp is described (Ng and Abelson, cit. above) which is in the same range. The RNA leader of Phaffia actin in front of the ATG was about ±115 bp.

By careful DNA analysis a putative ATG start codon was found. This postulated correct ATG was checked by PCR. Several oligo's situated in introns and exons in the regions of the presumed ATG were designed. The PCR was performed with the normal PCR protocol on RNA isolated from Phaffia. The results were DNA bands with different length (see Table 2).

TABLE 2

Results of the PCR experiments to identify the ATG start site of Phaffia actin.

| oligo's numbers | template DNA (bp) | PCR-band | template RNA (bp) | PCR-band |
| --- | --- | --- | --- | --- |
| 3457–3500 | 820 | yes | ? | no |
| 3457–3475 | 640 | yes | ±220 | no |
| 3457–3619 | 611 | yes | 176 | yes |
| 3457–3618 | 539 | yes | 164 | yes |

The oligo set 3457–3500 (SEQ ID NO: 7 and 9) situated on an assumed intron did not give a PCR band with RNA as a template. Oligo set 3457–3475 (SEQ ID NO: 7 and 8) was able to anneal to the cDNA according to the length of the RNA leader (5' primer extension) but did not give a PCR band with RNA as a template. The oligo's 3618 and 3619 (SEQ ID NO: 11 and 12) designed on the basis of an exon sequence anneal both with DNA and RNA as a template.

The actin gene has 4 introns (FIG. 3) and a length of 375 amino acids (for bp and aa sequence see SEQ ID NO: 13 and 14), this in contrast with the *K.lactis* and *S.cerevisiae* actin genes which have only 1 intron and consist of 375 amino acids and 374 amino acids respectively.

The homology with *K.lactis* actin is 85% on the protein level, but the 3' site is less homologous than the 5' site where only 5 amino acids out of the first 100 amino acids differ.

Example 8

Plasmid Constructions using the Actin Promoter

To avoid problems in making optimal constructs, having an exact connection between the promoter sequences and the marker gene(s) and cloning of Phaffia termination signals, we decided to construct fusion genes. In the literature such constructs have been described with G418 (Chen, X. J. and H. Fukuhara. 1988. Gene 69 181–192) and between the lac Z gene and the phleomycin gene (Baron et al. 1992. Gene 114: 239–243). These fusions expressed the marker gene very efficiently.

Cloning of the marker genes

Plasmid pGB-Ph1 was digested with BamHI or with XhoI, diluted and ligated to obtain plasmids which have different deletions in the structural actin gene. This resulted in plasmid pGB-Ph3 that has a BamHI deletion of 3246 bp. and plasmid pGB-Ph4 that has an XhoI deletion of 2048 bp. in the structural and 3' non coding sequences of the actin gene (see cloning diagrams in FIG. 4 and FIG. 5).

The plasmids pUCG418 and pUT701 were used as donor plasmids for the 1.1 Kb G418 BamHI fragment and the 0.9 Kb Phleo BamHI-BalII fragment respectively. The fragments were isolated by electrophoresis and agarase-treatment as described in the Experimental section.

The plasmids pGB-Ph3 and pGB-Ph4 were digested with BamHI and BglII respectively which are unique in these plasmids.

The Phleo fragment (including its own ATG startcodon) was ligated in the BamHI site at position 472 in the structural actin gene in pGB-Ph3 and the G418 fragment (including its own ATG startcodon) was ligated in the BglII site at position 934 of the structural actin gene in pGB-Ph4. After transformation to *E.coli*, colonies containing the plasmid of interest were screened by hybridization.

Restriction analyses revealed the expected plasmids pGB-Ph5 (G418) and pGB-Ph6 (phleo). Sequencing confirmed that the fusions were correct.

Cloning of the actin promoter in front of the fusion constructs

Plasmid pGB-Ph2, containing the actin promoter and further upstream sequences, and plasmid pGB-Ph5, containing the actin G418 fusion, were both digested with HindIII and SalI. The fragments of interest, i.e the 1.8 kb actin promoter and the 5.2 kb fusion-backbone fragment were isolated as described and ligated. This resulted in plasmid pGB-Ph7 (FIG. 5).

DNA isolated from *E.coli* transformants contained a plasmid with the expected length. Restriction analysis with HindIII x SalI , BamHI and EcoRV confirmed that the plasmid obtained was correct.

To obtain the Phleo construct, both plasmids pGB-Ph2 and pGB-Ph6 were digested with EcoRI and SAlI and the fragments, i.e the 1.4 kb fusion fragment and the 4.6 kb promoter-backbone fragment, were isolated and ligated. After transformation to *E.coli* DNA was isolated from randomly chosen colonies and analyzed by digestion with restriction enzymes. In this way the plasmid pGB-Ph8 was identified (FIG. 4).

Recloning the 3 kb SacI rDNA fragment of *P.rhodozyma*

To obtain plasmids containing other Phaffia sequences, we cloned a 3 kb SacI rDNA fragment leading to plasmid pGB-Ph11 as described above.

We reisolated the rDNA fragment from this plasmid and ligated it into the SacI digests of pGB-Ph7 and 8. After transformation to *E.coli* the plasmids pGB-Ph9 and 10 were isolated. For restriction map of plasmids pGB-Ph7 to 10 see FIGS. 4 and 5. (*E.coli* containing pGB-Ph9 was deposited at Centraal Bureau voor de Schimmelcultures in Baarn, The Netherlands on Jun. 23, 1993 under number CBS 359.93).

Example 9

Transformation Experiments using the Phaffia Actin Gene Fused to the Phleo Resistance Marker As can be seen in table 3 we were able to generate transformants with a very low frequency with the approach in which we used the Phaffia actin gene fused to the Phleo marker. Transformation was performed as described in Example 2 with the following modifications.

0.7M KCl–10 mM citric acid pH 6.2 was replaced by 1M sorbitol, incubation with Novozym 234 was between 10 and 20 min., plasmids were linearized before transformation, before plating the protoplasts were resuspended in 0.5 ml YePDS and incubated for 1–2 hours at room temperature, Protoplasts were diluted in 5 ml 0.7% low gelling temperature agarose/1M sorbitol (kept at 37° C.) and immediately poured on osmotically stabilised (1M sorbitol) selective agarplates.

Alternatively the protoplasts were plated on top of bilayer plates i.e. 15 ml YEPD bottom agar containing a selective amount of the required antibiotic and 1M sorbitol+after solidifying 15 ml YEPD agar containing 1M sorbitol without the antibiotic.

We also used a shorter protoplasting period which increased the regeneration from ±0.5% to 5–10%. To verify transformation we isolated total DNA (as described) from several transformants from five independent transformation experiments grown under selective conditions i.e in YEPD +0.1–0.2 µg phleomycin per ml.

TABLE 3

Number of transformants in different transformation experiments after 4–5 days incubation on selective agarplates (1 μg phleomycin/ml).

| DNA | Exp. 1 | Exp. 2 | Exp. 3 | Exp. 4 | Exp. 5* |
|---|---|---|---|---|---|
| pGB-Ph8 ccc | 19 | 6 | 1 | 5 | n.d |
| pGB-Ph8xSacI | 7 | 0 | 0 | n.d. | 1 |
| pGB-Ph10 ccc | n.d. | n.d. | n.d. | 9 | n.d. |
| — | 0 | 0 | 0 | 0 | 0 |

— = no DNA added, nd = not done, *= protoplasts not poured in agarose and selected on 5 μg/ml phleo on bilayer agar plates.

Chromosomal DNA was digested with both BamHI and EcoRI and after overnight electrophoresis blotted on nitrocellulose and hybridized with three different probes i.e pTZ18R, a 430 bp BamHI-StuI Phleo fragment and a 1.8 kb BamHI-SalI actin promoter fragment. As can be seen in FIG. 6A–6C three of the investigated DNA's show a specific signal with the pTZ18R probe and at least one DNA shows a clear signal with the Phleo probe. The actin probe shows the expected 2.2 kb band and some other inexplicable bands.

Example 10

Transformation of Total Phaffia DNA from Transformants to E.coli

E.coli JM 109 was transformed with the total DNA isolates of a number of transformants of Example 9. Surprisingly we found transformants in E.coli with some of the DNA samples. In one case we obtained transformants in E.coli with a total DNA preparation that shows no hybridization signal with respect to pTZ18R and Phleomycin. We isolated the plasmid DNA's by Qiagen method and analyzed them by restriction and hybridization.

The results show that we isolated plasmids that had been rearranged. In two out of three cases the plasmid contained more (of the same?) actin fragments and missed the Phleomycin sequence.

The total length was 11 kb which is ±5 kb longer than the plasmid that we used for the transformation. The third plasmid harboured no longer the Phleomycin and actin sequences and was 1 kb smaller.

It can be concluded that a structural instability exists of the Phleo plasmids which were transformed to Phaffia.

Example 11

Phaffia Transformation with Actin-G418 Fusions using the Lithium Method with Linearized Plasmids Several transformation experiments using the LiCl method, as it is used for transformation of S.cerevisiae and K.lactis were performed (see Experimental). The construct used was pGB-Ph7 linearized with EcoRV within the promoter sequence (FIG. 6A–6C).

Linearization was done in the promoter sequence to enable integration at the actin locus in the Phaffia genome. After transformation the cells were plated on YEPD plates with G418. The standard method gave. no transformants with Phaffia CBS 6938. Transformation was performed as described in Example 2 with the following modifications.

0.7M KCl–10 mM citric acid pH 6.2 was replaced by 1M sorbitol, incubation with Novozym 234 was between 10 and 20 min., plasmids were linearized before transformation, before plating the protoplasts were resuspended in 0.5 ml YePDS and incubated for 1–2 hours at room temperature, hygromycin was not used as selection marker.

Protoplasts were diluted in 5 ml 0.7% low gelling temperature agarose/1M sorbitol (kept at 37° C.) and immediately poured on osmotically stabilised (1M sorbitol) selective agarplates.

Alternatively the protoplasts were plated on top of bilayer plates i.e. 15 ml YEPD bottom agar containing a selective amount of the required antibiotic and 1M sorbitol+after solidifying 15 ml YEPD agar containing 1M sorbitol without the antibiotic.

It was decided to use the LiAc method (PLATE method, see Experimental) and to vary different factors in the protocol in this protocol the PEG and lithium incubation are carried out simultaneously and overnight or longer.

The following factors were varied;

G418 concentration, amount of cells,

DNA concentration, density of cells at harvesting,

YEPD incubation time.

The transformation experiments of Table 4 were performed with plasmid pGB-Ph9.

TABLE 4

Data for the transformation experiments using pGB-Ph9 and the PLATE method. A = $10^n$ cells/exp., B = $OD_{600}$, C = amount of DNA (plasmid), D = G418 concentration, E = YEPD incubation time, T = number of transformants.

| Run | A (n=) | B (OD) | C (μg) | D (μg/ml) | E (hr) | T (number) |
|---|---|---|---|---|---|---|
| 1 | 7 | 0.8 | 0 | 50 | 0 | 4 |
| 2 | 7 | 0.8 | 10 | 50 | 2 | 10 |
| 3 | 7 | 0.8 | 0 | 100 | 2 | 14 |
| 4 | 7 | 0.8 | 10 | 100 | 2 | 95 |

Cultures for chromosomal DNA isolates were made from;

2 colonies of CBS 6938

2 colonies of CBS 6938 without G418

2 colonies from run 1 (is negative control)

10 colonies from run 2

2 colonies from run 3 (is negative control)

10 colonies from run 4

All colonies were grown in 20 ml YEPD medium with 25 μg G418/ml (except for CBS 6938). After 4 days room temperature some of the colonies were not or hardly grown:

3a/3b (hardly)/4b/4d (hardly)/4i (hardly) /4j/CBS 6938 (on G418).

Chromosomal DNA isolates from all grown and slightly grown cultures were made. DNA from 2e was degraded. For the Southern blots all DNA's were digested with BamHI and blotted. This way 3 blots were made. They were hybridized with different probes.

Blot 1: PTZ-probe (FIG. 7A)

Blot 2: G418-probe (FIG. 7B)

Blot 3: rDNA-probe (FIG. 7C)

The results of the blots are shown in the figures.

The blot hybridized with PTZ-probe (FIG. 7A) should in case of transformants show a ±2.8 kb band. Of the 15 possible transformants on the blot 12 gave the right signal. The other 3 gave no signal at all. The 3 negative controls (CBS 6938, 1b and 3b) gave no signal.

The blot hybridized with G418-probe (FIG. 7B) should in case of transformants show a ±2.4 kb band. The same 12 as with the PTZ-probe gave the right band. The other 3 gave no signal. The negative controls also gave no signal.

If hybridized with rDNA-probe (FIG. 7C), the 12 DNAs which gave the right bands with the other two probes all show a ±8.5 kb band and a ±5.2 kb band. The other 3 and the negative controls only show a ±8.5 kb band as expected.

The plasmid (pGB-Ph9) used in the above transformation experiments contained the G418 gene under control of the Phaffia actin promoter. In addition this plasmid contains a Phaffia rDNA sequence. The high yield of transformants suggests that the plasmid is maintained extra-chromosomally. This suggests that the rDNA sequence contains an ARS. This would correspond with the finding that the rDNA sequence of S.cer. contains an ARS.

*Phaffia rhodozyma* transformed with pGB-Ph9 was deposited at Centraal Bureau voor de Schimmelcultures, Oosterstraat 1, PO Box 273, 3740 AG Baarn, the Netherlands on May 15, 1993 under number CBS 303.93.

SEQUENCE LISTING ( 1 ) GENERAL INFORMATION:

( i i i ) NUMBER OF SEQUENCES: 14

( 2 ) INFORMATION FOR SEQ ID NO: 1:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( C ) INDIVIDUAL ISOLATE: AB2192

( x i ) SEQUENCE DESCRIPTION: SEQ ID NO: 1:

GCCTGACTCG TCGACCTCGA GTTAGTTTCT AGAGTTGATG ATATCAAC        48

( 2 ) INFORMATION FOR SEQ ID NO: 2:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( C ) INDIVIDUAL ISOLATE: AB2193

( x i ) SEQUENCE DESCRIPTION: SEQ ID NO: 2:

CCCAGTCACG TCGACATGGC TAGAACTTTC TTTGTCGGTG GTAAC        45

( 2 ) INFORMATION FOR SEQ ID NO: 3:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( C ) INDIVIDUAL ISOLATE: AB2557

( x i ) SEQUENCE DESCRIPTION: SEQ ID NO: 3:

GCGCGGAATT CGGCATCACA CCTTCTACA        29

( 2 ) INFORMATION FOR SEQ ID NO: 4:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( C ) INDIVIDUAL ISOLATE: AB2558

( x i ) SEQUENCE DESCRIPTION: SEQ ID NO: 4:

CTTAAATTCT CAGGAATACA CAATACCAGT GGTTCT      36

( 2 ) INFORMATION FOR SEQ ID NO: 5:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( C ) INDIVIDUAL ISOLATE: AB3390

( x i ) SEQUENCE DESCRIPTION: SEQ ID NO: 5:

CGCCATCTTC TATAACAATA CC      22

( 2 ) INFORMATION FOR SEQ ID NO: 6:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( C ) INDIVIDUAL ISOLATE: AB3391

( x i ) SEQUENCE DESCRIPTION: SEQ ID NO: 6:

GCATCAAGGA GAAGCTCTGC TA      22

( 2 ) INFORMATION FOR SEQ ID NO: 7:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( C ) INDIVIDUAL ISOLATE: AB3457

( x i ) SEQUENCE DESCRIPTION: SEQ ID NO: 7:

ACGGCTCGGG GAGCATCATC TCCGGCG      27

(2) INFORMATION FOR SEQ ID NO: 8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: AB3475

(xi) SEQUENCE DESCRIPTION: SEQ ID NO: 8:

GTTACCGAAT TCCCTCTTTC TCTTCTTCCT     30

(2) INFORMATION FOR SEQ ID NO: 9:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: AB3500

(xi) SEQUENCE DESCRIPTION: SEQ ID NO: 9:

GATGGGATGG AAGATGCCT     19

(2) INFORMATION FOR SEQ ID NO: 10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: AB3538

(xi) SEQUENCE DESCRIPTION: SEQ ID NO: 10:

ACCGGCTTTA CACATACCAG AACCGTT     27

(2) INFORMATION FOR SEQ ID NO: 11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: AB3618

(xi) SEQUENCE DESCRIPTION: SEQ ID NO: 11:

ACAGTCTAGC CCACCAT     17

( 2 ) INFORMATION FOR SEQ ID NO: 12:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( C ) INDIVIDUAL ISOLATE: AB3619

( x i ) SEQUENCE DESCRIPTION: SEQ ID NO: 12:

GACCACCACT CACTCTTAC                                                                                 1 9

( 2 ) INFORMATION FOR SEQ ID NO: 13:

( i ) SEQUENCE CHARACTERISTICS:
        ( A ) LENGTH: 4320 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Phaffia rhodozyma
        ( B ) STRAIN: CBS 6938

( i x ) FEATURE:
        ( A ) NAME/KEY: exon
        ( B ) LOCATION: 581..582

( i x ) FEATURE:
        ( A ) NAME/KEY: intron
        ( B ) LOCATION: 583..920

( i x ) FEATURE:
        ( A ) NAME/KEY: exon
        ( B ) LOCATION: 921..942

( i x ) FEATURE:
        ( A ) NAME/KEY: intron
        ( B ) LOCATION: 943..1040

( i x ) FEATURE:
        ( A ) NAME/KEY: exon
        ( B ) LOCATION: 1041..1111

( i x ) FEATURE:
        ( A ) NAME/KEY: intron
        ( B ) LOCATION: 1112..1288

( i x ) FEATURE:
        ( A ) NAME/KEY: exon
        ( B ) LOCATION: 1289..1357

( i x ) FEATURE:
        ( A ) NAME/KEY: intron
        ( B ) LOCATION: 1358..1428

( i x ) FEATURE:
        ( A ) NAME/KEY: exon
        ( B ) LOCATION: 1429..2392

( i x ) FEATURE:
        ( A ) NAME/KEY: CDS
        ( B ) LOCATION: join(581..582, 921..942, 1041..1111,
                1289..1357, 1429..2392)
        ( D ) OTHER INFORMATION: /product="actin"

( x i ) SEQUENCE DESCRIPTION: SEQ ID NO: 13:

| | | | | | |
|---|---|---|---|---|---|
| AGCGATCGTA | AGATACAGGT | AACTAGCTAG | AGACACAAGA | AGAGATGTGT | GCATTGATGA | 60
| TCCTGAGCAT | AAGTTAGGCG | TACAAGAGCA | TTACAGCCTA | TATGTGAATG | GAAGTGAGAG | 120
| GTGGAAGTCA | GCCTCCAGAC | GAGTTGTACG | GTCTAATCAG | GGAAGAGCTG | GTCCAGAACC | 180
| AAATAAAATC | TTACTTCCGG | TGCCATATTA | ACTTAGATAA | AGGTATAAGA | TAGTATCGAT | 240
| TGAAATGACT | GTGTCTGTGA | GAAGATATGA | CTGAGAGCAC | ACAAGATGGG | ATGGAAGATG | 300
| CCTCTGTGGA | CTTGACTGAT | GGATTAGCTG | GAGGTCTAAC | CGCACGGCTT | AGTCAGCTAG | 360
| CCTTCACGTG | GTTACGACTG | CGATCGAATT | ATATTCTAAA | TTACAGCCGT | AATTTAGCCG | 420
| TCAACACAAC | CGTCCGTGCC | CAGGCCCCAT | CTCTTTATTT | CCCTCCTCTT | TCTCTTCTTC | 480
| CTTCCTTCTT | CCCGACCACC | ACTCACTCTT | ACTCTCTCTT | TCTCTCAAAA | CAAAACTCCC | 540
| GTACCTCCTC | CACCTTTAAA | AAGAAACAGT | CTAGCCCACC | AT | GTACGTCGAC | 592

Met
1

ATGCTTTCTT TCTCTTTCTG AAGTGTATGC GTGTGGTATT GTTATAGAAG ATGGCGATCG 652
GAAAGGCTCA TCGCCTCCTT TTTCTTTTTC ACTTCATCTG CGTTTCGCCT CTTTTTTTTT 712
TAAATCATCA TTTCTTCGTC TTTTTTGACA CTTGATTGTG CACTGCCCCT TTCTTTTTCT 772
CTTGCTTACG TCTTTCTCCT TCCCCGTCTT TGGATTTACC TCGGCCATCT TATAATCAAT 832
TCACTCTACC CTATTGACTG CGGCCTTATC ATCCATCCTT TTTTTTCCAT ATCGTGTGAT 892
GGATATGCGA TGGATTCTTC AACTCTAG G GAT GAT GAA GTT GCC GCC CTC 942

Asp Asp Glu Val Ala Ala Leu
                                                                                                    5

GTATGTGTTT CTAAATATCT TCATGATGCG AATTGGCTCC TTGGCTCATA TCCGCTTTCT 1002
TCGTTGTCTC TTGTAATGGT TTTCTTATCA TTCATTAG GTG ATT GAT AAC GGA 1055

Val Ile Asp Asn Gly
                                                                                                                                                          10

TCC GGA ATG TGC AAG GCC GGA TTC GCC GGA GAT GAT GCT CCC CGA GCC 1103
Ser Gly Met Cys Lys Ala Gly Phe Ala Gly Asp Asp Ala Pro Arg Ala
             15                      20                       25

GTC TTC CC GTAAGTACTA GTATCGTTTC GTCGAGCTTG GTTAAATTCA 1151
Val Phe Pro
      30

TGACAGAGCA AAAGCGATCC AAGAACATGC TTCACGTCTC AGTCTTGATA TTCGTAAAGA 1211
CGGAGTGGCA ACTCCTTGTA TGGATGACGC AACTGCTGAT CGTACCTCTT TCTGAATTGG 1271
TTAACCAATC TTCACAG C TCC ATT GTT GGA CGA CCC CGA CAC CAG GGT GTT 1322

Ser Ile Val Gly Arg Pro Arg His Gln Gly Val
                                            35                                       40

ATG GTC GGT ATG GGA CAG AAG GAC TCC TAC GTT GG GTTCGTATCT 1367
Met Val Gly Met Gly Gln Lys Asp Ser Tyr Val Gly
      45                    50                    55

TTCACATCTC TTGATGTCGT AACCGGCTCT TGTTATTAAC CTGATGTCTT CTATGCGGCA 1427
G T GAC GAG GCT CAG TCC AAG CGA GGT ATT CTT ACC CTC AAG TAC CCT 1474
    Asp Glu Ala Gln Ser Lys Arg Gly Ile Leu Thr Leu Lys Tyr Pro
                    60                                 65                              70

ATC GAG CAC GGA ATC GTC ACC AAT TGG GAC GAT ATG GAG AAG ATC TGG 1522
Ile Glu His Gly Ile Val Thr Asn Trp Asp Asp Met Glu Lys Ile Trp
                75                                 80                                 85

CAC CAC ACC TTT TAC AAC GAG CTT CGA GTT GCC CCT GAG GAG CAC CCC 1570
His His Thr Phe Tyr Asn Glu Leu Arg Val Ala Pro Glu Glu His Pro
                90                                 95                             100

| | | | | | | | | | | | | | | | | |
|---|---|---|---|---|---|---|---|---|---|---|---|---|---|---|---|---|
| GTC | CTT | CTT | ACT | GAG | GCT | CCT | CTA | AAC | CCC | AAG | GCT | AAC | AGA | GAG | AAG | 1618 |
| Val | Leu | Leu | Thr | Glu | Ala | Pro | Leu | Asn | Pro | Lys | Ala | Asn | Arg | Glu | Lys | |
| | | 105 | | | | | 110 | | | | | 115 | | | | |
| ATG | ACC | CAG | ATC | ATG | TTC | GAG | ACC | TTC | AAC | GCT | CCC | GCT | TTC | TAC | GTT | 1666 |
| Met | Thr | Gln | Ile | Met | Phe | Glu | Thr | Phe | Asn | Ala | Pro | Ala | Phe | Tyr | Val | |
| | 120 | | | | | 125 | | | | | 130 | | | | | |
| GCC | ATT | CAG | GCC | GTG | CTT | TCT | TTG | TAC | GCC | TCT | GGT | CGA | ACC | ACC | GGT | 1714 |
| Ala | Ile | Gln | Ala | Val | Leu | Ser | Leu | Tyr | Ala | Ser | Gly | Arg | Thr | Thr | Gly | |
| 135 | | | | | 140 | | | | | 145 | | | | | 150 | |
| ATC | GTG | CTC | GAC | TCT | GGA | GAC | GGA | GTC | AGT | CAC | ACT | GTT | CCT | ATC | TAC | 1762 |
| Ile | Val | Leu | Asp | Ser | Gly | Asp | Gly | Val | Ser | His | Thr | Val | Pro | Ile | Tyr | |
| | | | | 155 | | | | | 160 | | | | | 165 | | |
| GAG | GGT | TTC | GCC | CTT | CCC | CAC | GCC | ATC | CTC | CGA | TTG | GAC | TTG | GCC | GGT | 1810 |
| Glu | Gly | Phe | Ala | Leu | Pro | His | Ala | Ile | Leu | Arg | Leu | Asp | Leu | Ala | Gly | |
| | | | 170 | | | | | 175 | | | | | 180 | | | |
| CGA | GAC | TTG | ACC | GGG | TAC | CTT | GTC | AAG | TGC | TTG | ATG | GAG | CGA | GGA | TAC | 1858 |
| Arg | Asp | Leu | Thr | Gly | Tyr | Leu | Val | Lys | Cys | Leu | Met | Glu | Arg | Gly | Tyr | |
| | | 185 | | | | | 190 | | | | | 195 | | | | |
| CCT | TTC | ACC | ACC | ACT | GCC | GAG | CGA | GAG | ATT | GTT | CGA | GAC | ATC | AAG | GAG | 1906 |
| Pro | Phe | Thr | Thr | Thr | Ala | Glu | Arg | Glu | Ile | Val | Arg | Asp | Ile | Lys | Glu | |
| | 200 | | | | | 205 | | | | | 210 | | | | | |
| AAG | CTC | TGC | TAC | GTA | GCT | CTC | GAT | TTC | GAG | CAG | GAG | ATG | CAG | ACC | GCC | 1954 |
| Lys | Leu | Cys | Tyr | Val | Ala | Leu | Asp | Phe | Glu | Gln | Glu | Met | Gln | Thr | Ala | |
| 215 | | | | | 220 | | | | | 225 | | | | | 230 | |
| GCT | CAG | TCT | TCC | CAG | CTC | GAG | AAG | TCG | TAC | GAG | CTT | CCC | GAC | GGA | CAG | 2002 |
| Ala | Gln | Ser | Ser | Gln | Leu | Glu | Lys | Ser | Tyr | Glu | Leu | Pro | Asp | Gly | Gln | |
| | | | | 235 | | | | | 240 | | | | | 245 | | |
| GTT | ATC | ACC | ATT | GGA | AAC | GAG | CGA | TTC | CGA | TGC | CCT | GAA | GCT | CTC | TTC | 2050 |
| Val | Ile | Thr | Ile | Gly | Asn | Glu | Arg | Phe | Arg | Cys | Pro | Glu | Ala | Leu | Phe | |
| | | | 250 | | | | | 255 | | | | | 260 | | | |
| CAG | CCC | TCT | TTC | CTC | GGA | CTC | GAG | GCC | GCC | GGT | ATT | CAC | GAG | ACC | ACC | 2098 |
| Gln | Pro | Ser | Phe | Leu | Gly | Leu | Glu | Ala | Ala | Gly | Ile | His | Glu | Thr | Thr | |
| | | 265 | | | | | 270 | | | | | 275 | | | | |
| TAC | AAC | TCG | ATC | ATG | AAG | TGT | GAT | CTT | GAT | ATC | CGA | AAG | GAT | CTC | TAC | 2146 |
| Tyr | Asn | Ser | Ile | Met | Lys | Cys | Asp | Leu | Asp | Ile | Arg | Lys | Asp | Leu | Tyr | |
| | 280 | | | | | 285 | | | | | 290 | | | | | |
| GGA | AAC | GTC | GTC | CTT | TCC | GGA | GGA | ACC | ACC | ATG | TAC | TCT | GGT | ATT | GCC | 2194 |
| Gly | Asn | Val | Val | Leu | Ser | Gly | Gly | Thr | Thr | Met | Tyr | Ser | Gly | Ile | Ala | |
| 295 | | | | | 300 | | | | | 305 | | | | | 310 | |
| GAT | CGA | ATG | CAG | AAG | GAG | ATT | ACT | TCC | CTT | GCC | CCG | TCG | TCG | ATG | AAG | 2242 |
| Asp | Arg | Met | Gln | Lys | Glu | Ile | Thr | Ser | Leu | Ala | Pro | Ser | Ser | Met | Lys | |
| | | | | 315 | | | | | 320 | | | | | 325 | | |
| GTC | AAG | ATT | GTT | GCT | CCT | CCT | GAG | AGG | AAG | TAC | TCC | GTC | TGG | ATT | GGA | 2290 |
| Val | Lys | Ile | Val | Ala | Pro | Pro | Glu | Arg | Lys | Tyr | Ser | Val | Trp | Ile | Gly | |
| | | | 330 | | | | | 335 | | | | | 340 | | | |
| GGA | TCC | ATC | TTG | GCT | TCC | CTC | AGC | ACT | TTC | CAA | TCT | ATG | TGG | ATC | TCA | 2338 |
| Gly | Ser | Ile | Leu | Ala | Ser | Leu | Ser | Thr | Phe | Gln | Ser | Met | Trp | Ile | Ser | |
| | | 345 | | | | | 350 | | | | | 355 | | | | |
| AAG | CAG | GAG | TAC | GAC | GAG | GCT | GGA | CCT | TCC | ATC | GTC | CAC | CGA | AAG | TGC | 2386 |
| Lys | Gln | Glu | Tyr | Asp | Glu | Ala | Gly | Pro | Ser | Ile | Val | His | Arg | Lys | Cys | |
| | 360 | | | | | 365 | | | | | 370 | | | | | |
| TTC | TAAGTCAACA | AAGTCTTTCT | ATCCTTTAAG | GCAGAACGGT | TTCTTTTCTT | | | | | | | | | | | 2439 |
| Phe | | | | | | | | | | | | | | | | |
| 375 | | | | | | | | | | | | | | | | |

ACGATAGAGG CACCCTTGGC GGTCTTTCGC CAGCGGTGGT TTTCTCACTC TTTTTCCAAT 2499

ATTTTCACCG ACGTTTTTGC TCGCGTGTAT GTTTTTCTCT ACTTGATGCT ATCAATATCA 2559

TGGCTTTTAC GTTCCGTTGT ATTATCATCT TCTGCGCCCT TCTGACTGAG ATATCGAAAT 2619

CGTTACAACA CAAGACATAT AAAAATGAGA TTTATTCAAC TACTAAATAA CGATACATTA 2679

-continued

| | | | | | |
|---|---|---|---|---|---|
| GACGTAATAA | ATAGATTCAT | AGACAGGCCC | GAATGTTGAT | CGATCAAAGA | CTTTAAACGT | 2739
| AATTGCGACA | TTCTCCAAAA | CCCCAAGCCG | AACTCTTTCC | ATCACCTATT | TGTTCCCAAA | 2799
| TTTCGAAACA | TCCACTCTCT | TTCTGAAGCT | CAGTATCACC | TCGAGAACGG | ATCTTCAATC | 2859
| TTTAGGGCGT | GTCTTTTTCC | GGTCTTATCT | TGAATTTGTT | ATCGTCATTC | GATATAGATC | 2919
| TCCCTTATTG | TATTCTATCC | TTCGAACGCG | TTTTATACGT | ATCAACCCTC | GACCATGCCG | 2979
| TCCGATTCAT | CCCATCGAGC | CTCACGATCT | GGTTCATCAG | ACAAGAACAG | GTCGAATACA | 3039
| AACGGTCCAT | CAGCTCAGTC | TTCGTCTCTG | TTCTCCGGAT | CAGCTTCAGC | TCCGGCAGGT | 3099
| GCGTTGTTTT | CAGCGCCAGG | AACGCCGGTA | GAGGCAATCA | AGATTGATAT | GATTATCAGN | 3159
| TCAGCCGGAT | ATCCTTCCGC | CTGGGAATAT | CGAATTGCAT | CCTGAAGAGA | AGGGAAACTC | 3219
| GCAGTCAAAG | CAGAAAAATT | TACATCTATT | AAAAGAAAGA | ATGGANGACA | CCCCAAACGA | 3279
| GGTGAACCAC | GTTGAGGATT | TGGANGCGNA | NGNTANNGNG | AGTTCGCGTA | TCTCTGCGGC | 3339
| TACACAAGCG | GAGTCACCAA | ACCTTTCACT | CTTCATCCAC | TTCAAAGCCC | AGACACGAAC | 3399
| CCATGATACG | TCAAAGGATT | GAAGGACCAG | GAACAGAAGA | GGAAGAGGAA | GGGGAAGACC | 3459
| AAGCGCATCT | ACATGGACCA | GTAAAGAAGC | GAAGATTAGA | GCAAGAGCAA | GAAGGAAAGA | 3519
| AGATATTACT | GGATAAATTG | GAGCNGGCAG | GATTGACCAC | CGTCGATGGA | GGAGAGATAT | 3579
| CGGATGATCT | GCTAAAAGCC | CAGCTGGCGG | ATAGTATTGA | CTCTGCTGAT | TGGGTTCGTC | 3639
| CTCCCTTCTT | CTTCTCTGGG | TTCATCTTGC | CCCCTCCTCT | TCTAGAACAC | CTAGATGTTG | 3699
| TACAAATTGA | CTTCCTGTTG | TGTTATCATG | TCTGCGCGCT | CTTGAAACAG | GAAGATTTAT | 3759
| TAGAGAAAGA | GGAATCAGAA | CTTCAATCTT | ATGAAAGTAG | GCTAGATGAT | CTTCGGTGGT | 3819
| TTCAGTGGCA | GGGTATGTCG | CTCTTGTTTA | TCTCACAGTA | TGCATGGAAT | GTGTTTGTTG | 3879
| CTAAGTAGTT | CTTCTATCAA | TAACGCCTGT | GAATGTTCAG | CGATTAATCG | GTTTTCAGAT | 3939
| GAGGAGATCG | AAACAATGAC | GGCCTACTTG | AAAGAGAAAG | GTGAATCTCG | AGTATTGGAA | 3999
| AACGAGACAT | CAATAACCCT | CGAGTGCCTT | GCTGAGCATT | GTTTTCTTG | TTATTGTGGA | 4059
| TTGTGTGCTC | TCTTGAGGCT | TGTTGAATTT | TGTCAAGCGA | TATGTGATCG | AGCTGAAGTT | 4119
| CTCGGTACTT | CGGTTATTGA | ACGCTTTCCA | AATGAAGGTT | GTGCGTTTAA | ACTCTTCTAT | 4179
| CTTCTCACTT | CCGTTCGACG | TTACAGACCA | CATATCTGAC | TTGTTATACG | AACCTCTTTC | 4239
| TGTCTTCATT | TGGTATTGTT | TATTTAAATG | AACATCATAC | AACAGCCAAC | TTATTACAGG | 4299
| GATCCAAATC | TCGATGAATT | C | | | | 4320

( 2 ) INFORMATION FOR SEQ ID NO: 14:

( i ) SEQUENCE CHARACTERISTICS:
        ( A ) LENGTH: 375 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 14:

```
Met  Asp  Asp  Glu  Val  Ala  Ala  Leu  Val  Ile  Asp  Asn  Gly  Ser  Gly  Met
 1                 5                        10                       15

Cys  Lys  Ala  Gly  Phe  Ala  Gly  Asp  Asp  Ala  Pro  Arg  Ala  Val  Phe  Pro
                20                       25                       30

Ser  Ile  Val  Gly  Arg  Pro  Arg  His  Gln  Gly  Val  Met  Val  Gly  Met  Gly
               35                       40                       45

Gln  Lys  Asp  Ser  Tyr  Val  Gly  Asp  Glu  Ala  Gln  Ser  Lys  Arg  Gly  Ile
     50                       55                       60
```

-continued

| | | | | | | | | | | | | | | | |
|---|---|---|---|---|---|---|---|---|---|---|---|---|---|---|---|
| Leu<br>65 | Thr | Leu | Lys | Tyr | Pro<br>70 | Ile | Glu | His | Gly | Ile<br>75 | Val | Thr | Asn | Trp | Asp<br>80 |
| Asp | Met | Glu | Lys | Ile<br>85 | Trp | His | His | Thr | Phe<br>90 | Tyr | Asn | Glu | Leu | Arg<br>95 | Val |
| Ala | Pro | Glu | Glu<br>100 | His | Pro | Val | Leu | Leu<br>105 | Thr | Glu | Ala | Pro | Leu<br>110 | Asn | Pro |
| Lys | Ala | Asn<br>115 | Arg | Glu | Lys | Met | Thr<br>120 | Gln | Ile | Met | Phe | Glu<br>125 | Thr | Phe | Asn |
| Ala | Pro<br>130 | Ala | Phe | Tyr | Val | Ala<br>135 | Ile | Gln | Ala | Val | Leu<br>140 | Ser | Leu | Tyr | Ala |
| Ser<br>145 | Gly | Arg | Thr | Thr | Gly<br>150 | Ile | Val | Leu | Asp | Ser<br>155 | Gly | Asp | Gly | Val | Ser<br>160 |
| His | Thr | Val | Pro | Ile<br>165 | Tyr | Glu | Gly | Phe | Ala<br>170 | Leu | Pro | His | Ala | Ile<br>175 | Leu |
| Arg | Leu | Asp | Leu<br>180 | Ala | Gly | Arg | Asp | Leu<br>185 | Thr | Gly | Tyr | Leu | Val<br>190 | Lys | Cys |
| Leu | Met | Glu<br>195 | Arg | Gly | Tyr | Pro | Phe<br>200 | Thr | Thr | Thr | Ala | Glu<br>205 | Arg | Glu | Ile |
| Val | Arg<br>210 | Asp | Ile | Lys | Glu | Lys<br>215 | Leu | Cys | Tyr | Val | Ala<br>220 | Leu | Asp | Phe | Glu |
| Gln<br>225 | Glu | Met | Gln | Thr | Ala<br>230 | Ala | Gln | Ser | Ser | Gln<br>235 | Leu | Glu | Lys | Ser | Tyr<br>240 |
| Glu | Leu | Pro | Asp | Gly<br>245 | Gln | Val | Ile | Thr | Ile<br>250 | Gly | Asn | Glu | Arg | Phe<br>255 | Arg |
| Cys | Pro | Glu | Ala<br>260 | Leu | Phe | Gln | Pro | Ser<br>265 | Phe | Leu | Gly | Leu | Glu<br>270 | Ala | Ala |
| Gly | Ile | His<br>275 | Glu | Thr | Thr | Tyr | Asn<br>280 | Ser | Ile | Met | Lys | Cys<br>285 | Asp | Leu | Asp |
| Ile | Arg<br>290 | Lys | Asp | Leu | Tyr | Gly<br>295 | Asn | Val | Val | Leu | Ser<br>300 | Gly | Gly | Thr | Thr |
| Met<br>305 | Tyr | Ser | Gly | Ile | Ala<br>310 | Asp | Arg | Met | Gln | Lys<br>315 | Glu | Ile | Thr | Ser | Leu<br>320 |
| Ala | Pro | Ser | Ser | Met<br>325 | Lys | Val | Lys | Ile | Val<br>330 | Ala | Pro | Pro | Glu | Arg<br>335 | Lys |
| Tyr | Ser | Val | Trp<br>340 | Ile | Gly | Gly | Ser | Ile<br>345 | Leu | Ala | Ser | Leu | Ser<br>350 | Thr | Phe |
| Gln | Ser | Met<br>355 | Trp | Ile | Ser | Lys | Gln<br>360 | Glu | Tyr | Asp | Glu | Ala<br>365 | Gly | Pro | Ser |
| Ile | Val<br>370 | His | Arg | Lys | Cys | Phe<br>375 | | | | | | | | | |

I claim:

1. A Phaffia cell stably incorporating recombinant DNA to be expressed, which recombinant DNA comprises:
   a. a first DNA sequence to be expressed in said Phaffia cell;
   b. a Phaffia promoter, heterologous to said first DNA sequence and in operable linkage therewith, which promoter promotes detectable expression of said first DNA sequence; and
   c. a second DNA sequence which is homologous to a Phaffia chromosomal DNA sequence.

2. The Phaffis cell of claim 1, wherein said second DNA sequence is a ribosomal DNA sequence.

3. The Phaffia cell of claim 1, wherein said promotor is an actin promoter.

4. The Phaffia cell of claim 1, wherein said first DNA sequence comprises a selectable marker gene.

5. The Phaffia cell of claim 1, wherein said first or second DNA sequence encodes a protein that synthesizes a caroteniod precursor.

6. A method for producing transformed Phaffia cells, comprising:
   (a) preparing protoplasts from Phaffia cells which have been grown to exponential phase;
   (b) adding to the protoplasts recombinant DNA comprising:
       i. a first DNA sequence which is to be expressed in said cells,
       ii. a Phaffia promoter in operable linkage with said first DNA sequence, which promoter is heterologous to said first DNA sequence and promotes detectable expression of said first DNA sequence, and iii. a second DNA sequence which is homologous to a Phaffia chromosomal DNA sequence, (c) incubating the protoplasts to which said recombinant DNA has been added in a regeneration medium; and (d) selecting cells which have been transformed with said recombinant DNA, thereby producing said tranformed Phaffia cells.

7. The method according to claim 6, wherein said first DNA sequence comprises a selectable marker gene.

8. A method for expressing a recombinant DNA sequence in a Phaffia cell, comprising, (a) producing a transformed Phaffia cell according to the method of claim 7, and (b) growing said transformed Phaffia cell under conditions in which said first DNA sequence is expressed.

9. The method according to claim 6, wherein said first DNA sequence encodes a protein that synthesizes a carotenoid precursor.

10. The method of claim 6, wherein said second DNA sequence is a ribosomal DNA sequence.

11. A method for expressing a recombinant DNA sequence in a Phaffia cell, comprising, (a) producing a transformed Phaffia cell according to the method of claim 6; and (b) growing said transformed Phaffia cell under conditions in which said first DNA sequence is expressed.

12. A method for transforming Phaffia cells comprising:

(a) mixing Phaffia cells, in the presence of lithium acetate, with recombinant DNA comprising:
  i. a first DNA sequence which is to be expressed in said cells,
  ii. a Phaffia promoter in operable linkage with said first DNA sequence, which promoter is heterologous to said first DNA sequence and promotes detectable expression of said first DNA sequence, and
  iii. a second DNA sequence which is homologous to a Phaffia chromosomal DNA sequence, (b) incubating the mixture resulting from step (a) in a medium which promotes expression of said first DNA sequence; and (c) selecting cells which have been transformed with said recombinant DNA, thereby producing said transformed Phaffia cells.

13. The method according to claim 12, wherein said first DNA sequence comprises a selectable marker gene.

14. A method for expressing a recombinant DNA sequence in a Phaffia cell, comprising, (a) producing a transformed Phaffia cell according to the method of claim 13; and (b) growing said transformed Phaffia cell under conditions in which said first DNA sequence is expressed.

15. The method according to claim 12, wherein said first DNA sequence encodes a protein that synthesizes a carotenoid precursor.

16. A method for expressing a recombinant DNA sequence in a Phaffia cell, comprising, (a) producing a transformed Phaffia cell according to the method of claim 12; and (b) growing said transformed Phaffia cell under conditions in which said first DNA sequence is expressed.

17. A recombinant DNA molecule which is effective in producing a desired protein in a Phaffia cell, comprising:

(a) a first DNA sequence encoding the desired protein;

(b) in operable linkage with said first DNA sequence, a Phaffia promoter heterologous to said DNA sequence; and (c) a second DNA sequence which is homologous to a Phaffia chromosomal DNA sequence.

18. The recombinant DNA molecule of claim 17 which further includes a selectable marker gene operable in Phaffia.

19. The recombinant DNA molecule of claim 17, wherein said desired protein is the product of a selectable marker gene operable in Phaffia.

20. The DNA molecule of claim 17, wherein said second DNA sequence is a ribosomal DNA sequence.

* * * * *